(12) United States Patent
Ghosh et al.

(10) Patent No.: US 8,682,436 B2
(45) Date of Patent: Mar. 25, 2014

(54) DETECTION OF TARGET VEIN FOR CRT THERAPY

(75) Inventors: Subham Ghosh, Circle Pines, MN (US); Jeffrey M. Gillberg, Coon Rapids, MN (US); Nathan A. Grenz, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 115 days.

(21) Appl. No.: 13/336,113

(22) Filed: Dec. 23, 2011

(65) Prior Publication Data
US 2013/0165986 A1  Jun. 27, 2013

(51) Int. Cl.
*A61N 1/00* (2006.01)

(52) U.S. Cl.
USPC .......................................................... 607/28

(58) Field of Classification Search
USPC ............................ 607/28, 27; 600/509, 513
See application file for complete search history.

(56) References Cited

U.S. PATENT DOCUMENTS

| | | | |
|---|---|---|---|
| 6,978,184 B1 | 12/2005 | Marcus et al. | |
| 7,142,922 B2 | 11/2006 | Spinelli et al. | |
| 7,751,882 B1 | 7/2010 | Helland | |
| 7,769,451 B2 | 8/2010 | Yang et al. | |
| 7,818,040 B2 | 10/2010 | Spear et al. | |
| 7,953,482 B2 | 5/2011 | Hess | |
| 8,265,738 B1 * | 9/2012 | Min et al. | 600/509 |
| 2005/0149138 A1 * | 7/2005 | Min et al. | 607/27 |
| 2006/0224198 A1 | 10/2006 | Dong et al. | |
| 2008/0306567 A1 | 12/2008 | Park et al. | |
| 2009/0270937 A1 | 10/2009 | Yonce et al. | |
| 2010/0049063 A1 | 2/2010 | Dobak, III | |
| 2011/0213260 A1 * | 9/2011 | Keel et al. | 600/513 |

OTHER PUBLICATIONS

Ghosh et al., "Cardiac Memory in Patients with Wolff-Parkinson-White Syndrome: Noninvasive Imaging of Activation and Repolarization Before and After Catheter Ablation" *Circulation*, 2008; 118:907-915. Published online Aug. 12, 2008.
Gold et al., "Comparison of stimulation sites within left ventricular veins on the acute hemodynamic effects of cardiac resynchronization therapy" *Heart Rhythm*, Apr. 2005; 2(4):376-381.
Steinhaus, "Estimating Cardiac Transmembrane Activation and Recovery Times from Unipolar and Bipolar Extracellular Electrograms: A Simulation Study" *Circulation Research*, 1989, 64:449-462.

* cited by examiner

*Primary Examiner* — Robert N Wieland
(74) *Attorney, Agent, or Firm* — Carol F. Barry

(57) ABSTRACT

A method for selecting a target vein for left ventricular lead placement for cardiac resynchronization therapy includes determining electrical dispersion for the first coronary vein by calculating the difference between (i) activation time at a location of the vein that has the latest activation time of a plurality of locations in the vein and (ii) activation time at a location that has the earliest activation time of the plurality of locations. The method may further include (ii) determining whether the magnitude of the electrical dispersion for the vein meets or exceeds a predetermined threshold selecting the vein if the vein meets or exceeds the predetermined threshold; or (ii) selecting, among several veins, the vein that has the highest electrical dispersion.

20 Claims, 16 Drawing Sheets

DETECTION OF TARGET VEIN FOR CRT THERAPY

FIELD

The present disclosure relates to, among other things, methods, devices and systems for selecting a target vein for left ventricle pacing in cardiac resynchronization therapy (CRT).

BACKGROUND

Implantable devices that provide electrical stimulation to selected chambers of the heart have been developed in order to treat a number of cardiac disorders. A pacemaker, for example, is a device which paces the heart with timed pacing pulses, most commonly for the treatment of bradycardia where the ventricular rate is too slow. Implantable devices may also be used to treat cardiac rhythms that are too fast, with either anti-tachycardia pacing or the delivery of electrical shocks to terminate atrial or ventricular fibrillation.

Implantable devices have also been developed that affect the manner and degree to which the heart chambers contract during a cardiac cycle in order to promote the efficient pumping of blood. In a properly functioning heart, contraction of each atrium or ventricle is synchronized with the contralateral atrium or ventricle. Without such synchronization, the heart's pumping efficiency is greatly diminished. To treat patients suffering from inefficient or unsynchronized pumping of the heart, CRT devices, which provide appropriately timed electrical stimulation to one or more heart chambers in an attempt to improve the coordination of atrial or ventricular contractions, have been developed.

A common form of CRT applies stimulation pulses to both ventricles, either simultaneously or separated by a specified biventricular offset interval, and after a programmed atrioventricular (AV) delay interval with respect to the detection an intrinsic atrial contraction or delivery of an atrial pace. With such CRT, an electrode of a right ventricular lead is placed in contact with the right ventricle, typically at the apical wall, and a left ventricular lead containing an electrode for pacing the left ventricle is typically placed in a vein of the coronary sinus overlying the left ventricle.

Site selection for coronary sinus (CS) left ventricular (LV) lead placement, whether for biventricular pacing or for left ventricular pacing, may be important for effecting patient response to CRT. One criteria that has been proposed for CS LV lead placement is electrical timing of the CS sites, where the latest site of electrical activation has been proposed as being the best site for placement of the LV lead. However, there appears to be little or no data supporting the idea that lateness of electrical activation during intrinsic or paced rhythms will predict a site for LV lead placement that will result in a favorable response to CRT.

SUMMARY

In the present disclosure, studies are described which show poor correlation between lateness of activation and effectiveness of CRT when CS LV electrodes are in the vein at the location of latest activation. However, strong correlation is shown between veins with high electrical dispersion, e.g. the difference between the latest activation time and the earliest activation time at multiple locations within the vein, and CRT mediated pumping efficiency when CS LV electrodes are positioned in a vein with high electrical dispersion. Among other things, methods, systems and devices for selecting a target vein for CRT therapy employing such electrical dispersion determinations are described herein.

In embodiments, a method for selecting a target vein for left ventricular lead placement for cardiac resynchronization therapy is described herein. The method includes marking timing of a fiducial of electrical activity of the heart and determining a myocardial activation time, relative to the timing of the fiducial, at each of a plurality of locations in or along a coronary vein overlying a left ventricle. The method further includes determining an electrical dispersion for the coronary vein. Determining the electrical dispersion comprises calculating the difference between (i) the activation time at the location that had the latest activation time of the plurality of locations and (ii) the activation time at the location that had the earliest activation time of the plurality of locations; and determining whether the magnitude of the electrical dispersion for the vein meets or exceeds a predetermined high threshold. The method also includes identifying the vein as the target vein for left ventricular lead placement if the electrical dispersion for the vein meets or exceeds the predetermined high threshold.

In embodiments, a method carried out by a device configured to assist in selecting a target vein for left ventricular lead placement for cardiac resynchronization therapy is described herein. The method includes receiving input regarding timing of a fiducial of electrical activity of the heart; receiving input regarding local electrical activity at a plurality of locations in or along a coronary vein overlaying a left ventricle; and determining a myocardial activation time, relative to the timing of the fiducial, of each of the plurality of locations in or along the coronary vein. The method further includes determining an electrical dispersion for the coronary vein. Determining the electrical dispersion comprises calculating the difference between (i) the activation time at the location that had the latest activation time of the plurality of locations and (ii) the activation time at the location that had the earliest activation time of the plurality of locations. The method also includes determining whether the magnitude of the electrical dispersion for the vein meets or exceeds a predetermined threshold.

In embodiments, a computer readable medium for a system configured to identify a target vein for left ventricular lead placement for cardiac resynchronization therapy is described herein. The computer readable medium comprising instructions that, when implemented, cause the system to: (a) mark timing of a fiducial of electrical activity of the heart; (b) determine a myocardial activation time, relative to the timing of the fiducial, at each of a plurality of locations in or along a coronary vein overlying a left ventricle; (c) determine an electrical dispersion for the coronary vein by calculating the difference between (i) the activation time at the location that had the latest activation time of the plurality of locations and (ii) the activation time at the location that had the earliest activation time of the plurality of locations; (d) determine whether the magnitude of the electrical dispersion for the vein meets or exceeds a predetermined threshold; and (e) indicate the vein as the target vein for left ventricular lead placement if the electrical dispersion for the vein meets or exceeds a predetermined threshold. Systems and devices including the computer readable medium are also described herein.

In embodiments, a system is described herein. The system includes (a) means for marking timing of a fiducial of electrical activity of the heart; (b) means for determining a myocardial activation time, relative to the timing of the fiducial, at each of a plurality of locations in or along a coronary vein overlying a left ventricle; (c) means for determining an electrical dispersion for the coronary vein, wherein determining the electrical dispersion comprises calculating the difference between (i) the activation time at the location that had the latest activation time of the plurality of locations and (ii) the activation time at the location that had the earliest activation time of the plurality of locations; (d) means for determining whether the magnitude of the electrical dispersion for the vein meets or exceeds a predetermined threshold; and (e) means for indicating the vein as the target vein for left ventricular lead placement if the electrical dispersion for the vein meets or exceeds a predetermined threshold.

In embodiments, a method for selecting a target vein for left ventricular lead placement for cardiac resynchronization therapy is described herein. The method includes (a) marking timing of a fiducial of electrical activity of the heart; (b) determining a myocardial activation time, relative to the timing of the fiducial, at each of a plurality of locations in or along a first coronary vein overlying a left ventricle; (c) determining an electrical dispersion for the first coronary vein, wherein determining the electrical dispersion comprises calculating the difference between (i) the activation time at the location that had the latest activation time of the plurality of locations and (ii) the activation time at the location that had the earliest activation time of the plurality of locations; (d) determining a myocardial activation time, relative to the timing of the fiducial, at each of a plurality of locations in or along a second coronary vein overlying a left ventricle; (e) determining an electrical dispersion for the second coronary vein, wherein determining the electrical dispersion comprises calculating the difference between (i) the activation time at the location that had the latest activation time of the plurality of locations and (ii) the activation time at the location that had the earliest activation time of the plurality of locations; (f) determining whether the magnitude of the electrical dispersion for the first vein is greater than the electrical dispersion for the second vein; and (g) identifying the first vein as the target vein for left ventricular lead placement if the electrical dispersion for the first vein is greater than the electrical dispersion for the second vein.

One or more of the embodiments of one or more method, computer readable medium, device or system described herein may have one or more advantages relative to existing methods, computer readable media, devices or systems for CRT. One skilled in the art will appreciate these advantages upon reading the description and drawings that follow.

BRIEF DESCRIPTION OF THE DRAWINGS

The accompanying drawings, which are incorporated into and form a part of the specification, illustrate several embodiments of the present disclosure and, together with the description, serve to explain the principles of the disclosure. The drawings are only for the purpose of illustrating embodiments of the disclosure and are not to be construed as limiting the disclosure.

Figure 1:
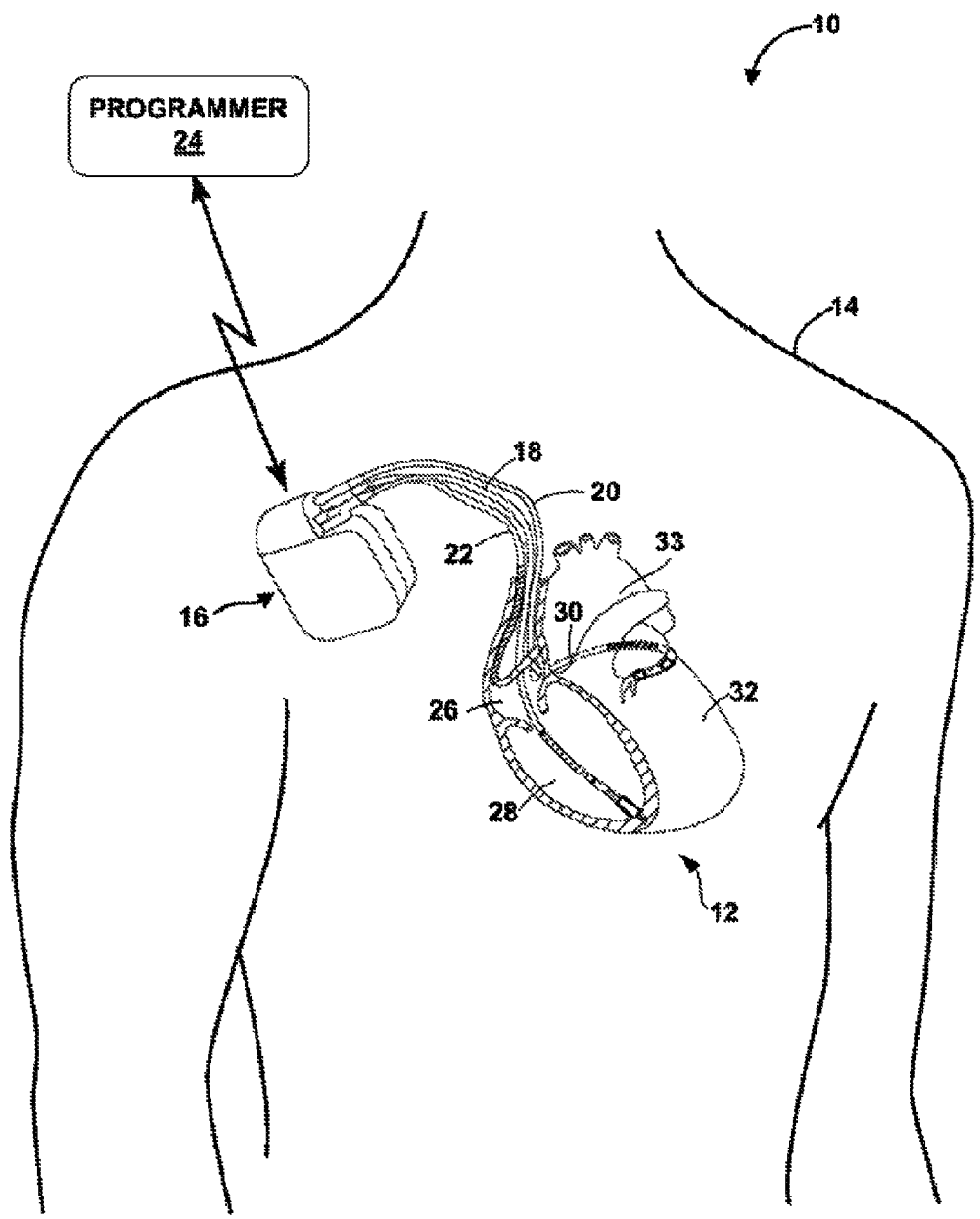
FIG. 1 is a schematic conceptual diagram illustrating an example therapy system that may be used to provide therapy to heart of patient.

The schematic drawings presented herein are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to."

"Consisting essentially of", as it relates to a device, system, or method, means that the device, system, or method includes only the recited components or steps of the device, system, or method and, optionally, other components or steps that do not materially affect the basic and novel properties of the device, system, or methods.

"Consisting of" and "consisting essentially of" are subsumed within "comprising."

Any direction referred to herein, such as "top," "bottom," "left," "right," "upper," "lower," "above," "below," and other directions and orientations are described herein for clarity in reference to the figures and are not to be limiting of an actual device or system or use of the device or system. Many of the devices or systems described herein may be used in a number of directions and orientations.

The present disclosure relates to, among other things, methods, devices and systems for selecting a target vein for left ventricle pacing in cardiac resynchronization therapy (CRT). An estimated 30-40% of CRT patients do not favorably respond to CRT. Accordingly, methods, devices and systems that can improve patient response may be important. One factor for favorable CRT response may be the choice of placement of the left ventricular (LV) lead. Electrical mapping of intrinsic conduction and selection of the latest activation times has been previously suggested as a roadmap for deciding the location of a LV lead. However, as described herein, the relationship between mere electrical activation timing and acute response to pacing is not consistent and exhibits both intra- and inter-patient variability. As further described herein, an approach for guiding the LV lead to the area with a high degree of electrical dispersion (or dyssynchrony), rather than high absolute values of activation timing, may result in better CRT responses.

In embodiments, the timing of local electrical activity at a plurality of locations in or along a coronary sinus vein is determined relative to a fiducial of electrical activity of the heart. Among the plurality of locations, which is typically three of more, the location of maximum relative timing of the local electrical activity (the latest location) and the location of minimum relative timing of electrical activity (the earliest location) may be identified. The difference of the timing of the electrical activity at the latest location (max time) and the timing of the electrical activity of the earliest location (min time) is calculated to determine the electrical dispersion (ED) for the vein as shown below in Equation 1.

$$ED = \text{max time} - \text{min time} \quad \text{Equation 1}$$

In embodiments, electrical dispersion (ED) of multiple coronary sinus veins is determined, and the coronary sinus vein with the largest electrical dispersion is selected as the target vein for placement of the left ventricular lead. In embodiments, a vein is selected as the target vein for placement of the left ventricular lead if the electrical dispersion meets or exceeds a predetermined threshold.

Any suitable local electrical activity may be sensed or detected for purposes of determining electrical dispersion. In embodiments, the local electrical activity is depolarization or myocardial activation. Myocardial activation may be detected by monitoring the change in a local electrogram (egm) over time ($\delta[\text{egm}]/\delta t$) to detect electrical activity indicative of activation. Any suitable algorithm for detecting signals indicative of local myocardial activation may be employed. Such algorithms are well known in the art. For example, the algorithms described in Steinhaus B M., 1989, "Estimating cardiac transmembrane activation and recovery times from unipolar and bipolar extracellular electrograms: a simulation study," Circulation Research, 64:449-462 may be used for purposes of detecting myocardial activation and timing of myocardial activation.

Local electrical activity, such as myocardial activation, may be monitored in any suitable manner. In embodiments, a lead having one or more recording electrodes is placed in a coronary vein for purposes of monitoring the local electrical activity. In embodiments, local electrical activity is monitored noninvasively. For example, local activation times may be determined from electrical activity sensed at an array of electrodes positioned about a patient's skin and employing appropriate algorithms and imaging methodologies to identify local activation times. Some representative non-limiting examples of literature in which such algorithms and imaging methodologies are described include (i) Ghosh S et al 2008. Cardiac memory in WPW Patients: noninvasive imaging of activation and repolarization before and after catheter ablation, Circulation 118:907-915. ii) Modre et al., 2002, "Noninvasive myocardial activation time imaging: A novel inverse algorithm applied to clinical ECG mapping data," IEEE Transactions on Biomedical Engineering, 49 (10): 1153-1161; (iii) He et al., 2002, "Non-invasive three-dimensional activation time imaging of ventricular excitation by means of a heart-excitation model," Phys. Med. Biol. 47: 4063-4078; (iv) Zhang et al., 2005, "Noninvasive three-dimensional electrocardiographic imaging of ventricular activation sequence," Am. J. Physiol. Heart Circ. Physiol. 289: H2724-H2732; and (v) Modre et al., 2001, "An iterative algorithm for myocardial activation time imaging," Computer Methods and Programs in Biomedicine, 64(1): 1-7. The noninvasively obtained mapped activation times may be overlaid on an image of the coronary veins of the heart to determine activation times in or along coronary veins of the left ventricle. The coronary veins may be imaged via any suitable process, such as fluoroimaging, MRI or the like.

Regardless of whether determined invasively or non-invasively, local electrical activity or activation time is determined relative to timing of a fiducial. The fiducial may be an indicator of a global cardiac event, such as timing of contraction of a chamber of the heart; timing of pacing of a chamber of the heart; or the like. For example, the fiducial may be the onset of QRS, the peak of QRS, onset of application of a pacing electrical stimulus, or the like.

Fiducial electrical activity may be sensed by one or more electrodes, which may be the same or different from electrodes employed for purposes of detecting local electrical activity. In embodiments, fiducial electrical activity is detected by the implantable CRT system. In embodiments, fiducial electrical activity is detected by a monitoring device, which may be implanted or wearable or otherwise external to the patient, such as a Holter monitoring device. Of course, any suitable mechanism of detecting or marking timing of a fiducial may be employed.

In embodiments, the timing of the fiducial equates to the timing of delivery of a pacing signal to a chamber of the heart. The timing may be the initiation of the pacing signal or the like. The device delivering the pacing signal may include appropriate electronics to track and mark the timing of the pacing signal, which marked or tracked time may be used for purposes of determining local activation time and electrical dispersion as discussed above. The device that delivers the pacing signal may be a device configured for delivering CRT.

Determination of electrical dispersion within or along a vein may be performed by a device, such as a device configured to deliver CRT, or a system employing more than one device. If multiple devices are employed; e.g., one for monitoring the fiducial and one for monitoring the local electrical activity in or along a vein, the system should be configured such that the relative timing of the local activity to the timing of the fiducial may be determined. If a single device is used to monitor the fiducial and the local activity, an internal clock, or the like, of the device may be used to coordinate timing of the fiducial relative to the local activity.

Prior to describing the methods, processes or algorithms for monitoring electrical dispersion in or along a left ventricular coronary vein for purposes of selecting a target vein for CRT, a discussion of devices and systems for delivering CRT is provided below. Common forms of CRT include biventricular CRT, in which both ventricles are stimulated, either simultaneously or separated by a ventricular offset interval, and left ventricular only CRT in which the left ventricle is stimulated and right ventricular contractions are initiated by intrinsic beating of the heart. Whether CRT pacing is biventricular or left ventricular, pacing is initiated after a programmed atrio-ventricular (AV) delay interval with respect the detection of an intrinsic atrial contraction or delivery of an atrial pace. Typically, the left ventricular lead containing an electrode for pacing the left ventricle is placed in a vein of the coronary sinus overlaying the left ventricle.

1. Overview of Devices and Systems

One exemplary system that may be used for CRT is depicted in the conceptual schematic diagram of FIG. 1. Therapy system 10 of FIG. 1 is configured to provide CRT to heart 12 of patient 14. Patient 12 ordinarily, but not necessarily, will be a human. Therapy system 10 includes an active implantable electrical medical (IMD) 16, which is coupled to leads 18, 20, and 22, and programmer 24. IMD 16 provides electrical signals to, or senses electrical signals from, heart 12 via electrodes coupled to one or more of leads 18, 20, and 22.

In the embodiment depicted in FIG. 1, leads 18, 20, 22 extend into the heart 12 of patient 16 to sense electrical activity of heart 12 or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12 via a vein branching from the coronary sinus. Right atrial (RA) lead 22 extends through one or more veins and the vena cava, and into the right atrium 26 of heart 12.

IMD 16 may sense electrical signals attendant to the depolarization and repolarization of heart 12 via electrodes (not shown in FIG. 1) coupled to at least one of the leads 18, 20, 22. IMD 16 may also provide pacing pulses to heart 12 based on the electrical signals sensed within heart 12. The configurations of electrodes used by IMD 16 for sensing and pacing may be unipolar or bipolar. IMD 16 may, in some embodiments, also provide defibrillation therapy and/or cardioversion therapy via electrodes located on at least one of the leads 18, 20, 22.

Programmer 24 may be a handheld computing device, a computer workstation, or the like. Programmer 24 may include a user interface that receives input from a user. The user interface may include, for example, a keypad and a display. The keypad may take the form of an alphanumeric keypad or a reduced set of keys associated with particular functions. Programmer 24 can additionally or alternatively include a peripheral pointing device, such as a mouse, via which a user may interact with the user interface. In some embodiments, a display of programmer 24 may include a touch screen display, and a user may interact with programmer 24 via the display.

A user, such as a physician, technician, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD.

For example, the user may use programmer 24 to retrieve information from IMD 16 regarding the rhythm of heart 12, trends therein over time, tachyarrhythmia episodes, or the like. As another example, the user may use programmer 24 to retrieve information from IMD 16 regarding sensed physiological parameters of patient 14, such as intracardiac or intravascular pressure, activity, posture, respiration, thoracic impedance, or the like (if device is so equipped). As another example, the user may use programmer 24 to retrieve information from IMD 16 regarding the performance or integrity of IMD 16 or other components of system 10, such as leads 18, 20, and 22, a power source of IMD 16, or the like.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

Figure 2:
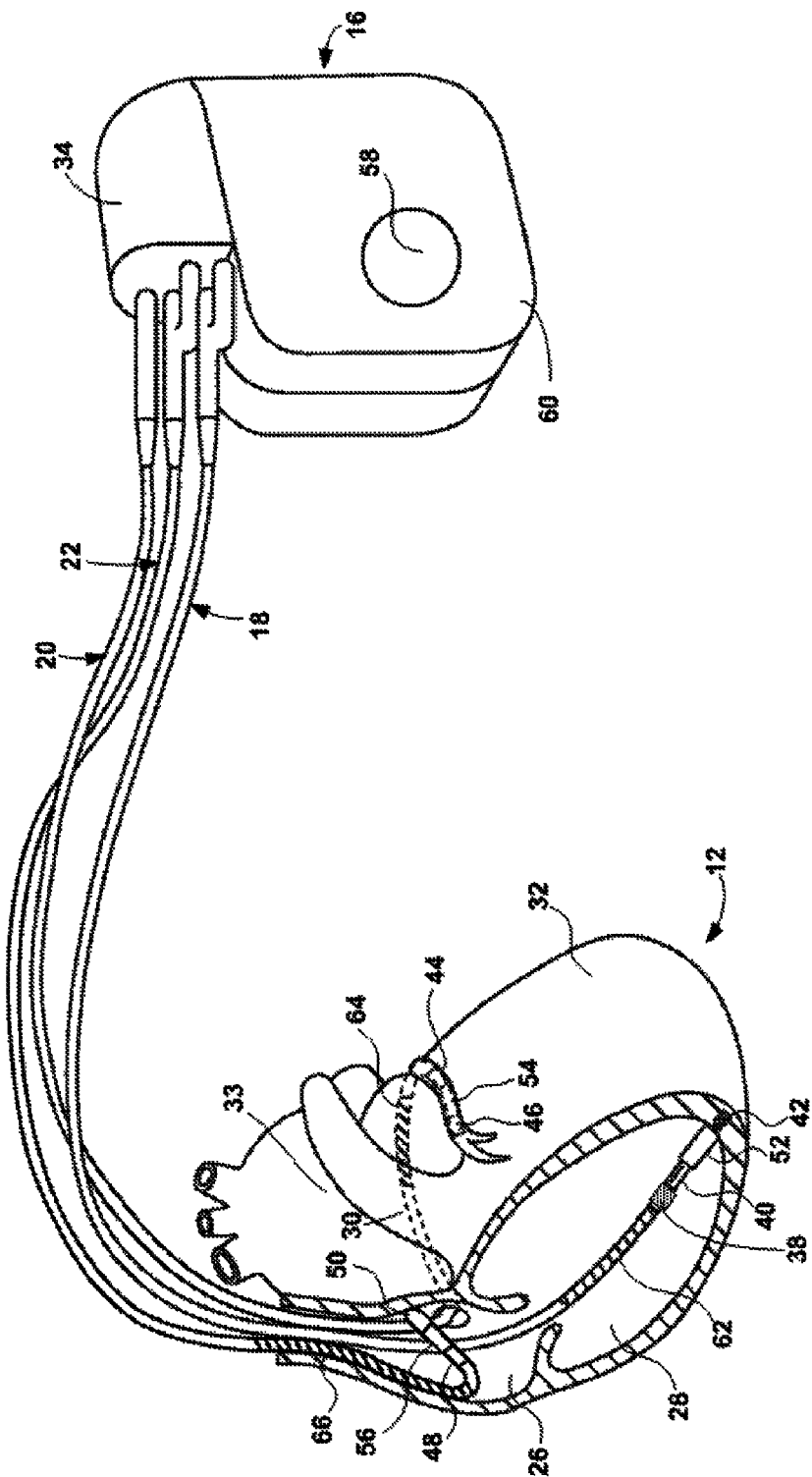
FIG. 2 is a schematic conceptual diagram illustrating an example therapy system that may be used to provide therapy to heart of patient.

FIG. 2 is a conceptual schematic diagram of an embodiment of the system 10 depicted in FIG. 1 illustrating IMD 16 and leads 18, 20, 22 of therapy system 10 in greater detail. Leads 18, 20, 22 may be electrically coupled to a stimulation generator, a sensing module, or other modules IMD 16 via connector block 34. In some examples, proximal ends of leads 18, 20, 22 may include electrical contacts that electrically couple to respective electrical contacts within connector block 34. In addition, in some examples, leads 18, 20, 22 may be mechanically coupled to connector block 34 with the aid of set screws, connection pins or another suitable mechanical coupling mechanism.

Each of the leads 18, 20, 22 includes an elongated insulative lead body, which may carry a number of concentric coiled conductors separated from one another by tubular insulative sheaths. In the illustrated example, an optional pressure sensor 38, such as a capacitive or piezoelectric absolute pressure sensor, and bipolar electrodes 40 and 42 are located proximate to a distal end of lead 18. In addition, bipolar electrodes 44 and 46 are located proximate to a distal end of lead 20 and bipolar electrodes 48 and 50 are located proximate to a distal end of lead 22.

Electrodes 40, 44 and 48 may take the form of ring electrodes, and electrodes 42, 46 and 50 may take the form of extendable helix tip electrodes mounted retractably within insulative electrode heads 52, 54 and 56, respectively. Each of the electrodes 40, 42, 44, 46, 48 and 50 may be electrically coupled to a respective one of the coiled conductors within the lead body of its associated lead 18, 20, 22, and thereby coupled to respective ones of the electrical contacts on the proximal end of leads 18, 20 and 22.

Electrodes 40, 42, 44, 46, 48 and 50 may sense electrical signals attendant to the depolarization and repolarization of heart 12. The electrical signals are conducted to IMD 16 via the respective leads 18, 20, 22. IMD 16 may also deliver pacing pulses via electrodes 40, 42, 44, 46, 48 and 50 to cause depolarization of cardiac tissue of heart 12. In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. Any of the electrodes 40, 42, 44, 46, 48 and 50 may be used for unipolar sensing or pacing in combination with housing electrode 58. As described in further detail with reference to FIG. 3, housing 60 may enclose a stimulation generator that generates cardiac pacing pulses, as well as a sensing module for monitoring the patient's heart rhythm.

Leads 18, 20, 22 may also include elongated electrodes 62, 64, 66, respectively, which may take the form of a coil. IMD 16 may deliver defibrillation shocks to heart 12 via any combination of elongated electrodes 62, 64, 66, and housing electrode 58. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy or other materials known to be usable in implantable defibrillation electrodes.

The configuration of therapy system 10 illustrated in FIGS. 1 and 2 is merely one example. In other examples, a therapy system may include epicardial leads and/or patch electrodes instead of or in addition to the transvenous leads 18, 20, 22 illustrated in FIG. 1. Further, IMD 16 need not be implanted within patient 14. In examples in which IMD 16 is not implanted in patient 14, IMD 16 may deliver defibrillation shocks and other therapies to heart 12 via percutaneous leads that extend through the skin of patient 14 to a variety of positions within or outside of heart 12.

In other examples of therapy systems that provide electrical stimulation therapy to heart 12, a therapy system may include any suitable number of leads coupled to IMD 16, and each of the leads may extend to any location within or proximate to heart 12. For example, other examples of therapy systems may include three transvenous leads located as illustrated in FIGS. 1 and 2, and an additional lead located within or proximate to left atrium 33. As another example, other examples of therapy systems may include a single lead that extends from IMD 16 into right atrium 26 or right ventricle 28, or two leads that extend into a respective one of the right ventricle 26 and right atrium 28.

For biventricular CRT, IMD 16 applies pacing stimulus via left ventricular lead 20 and right ventricular lead 18, and may apply pacing via atrial lead 22. For left ventricular CRT, IMD 16 applies pacing via left ventricular lead 20. In such cases, the right ventricular lead 18 may be omitted or inactive, if implanted.

Figure 3:
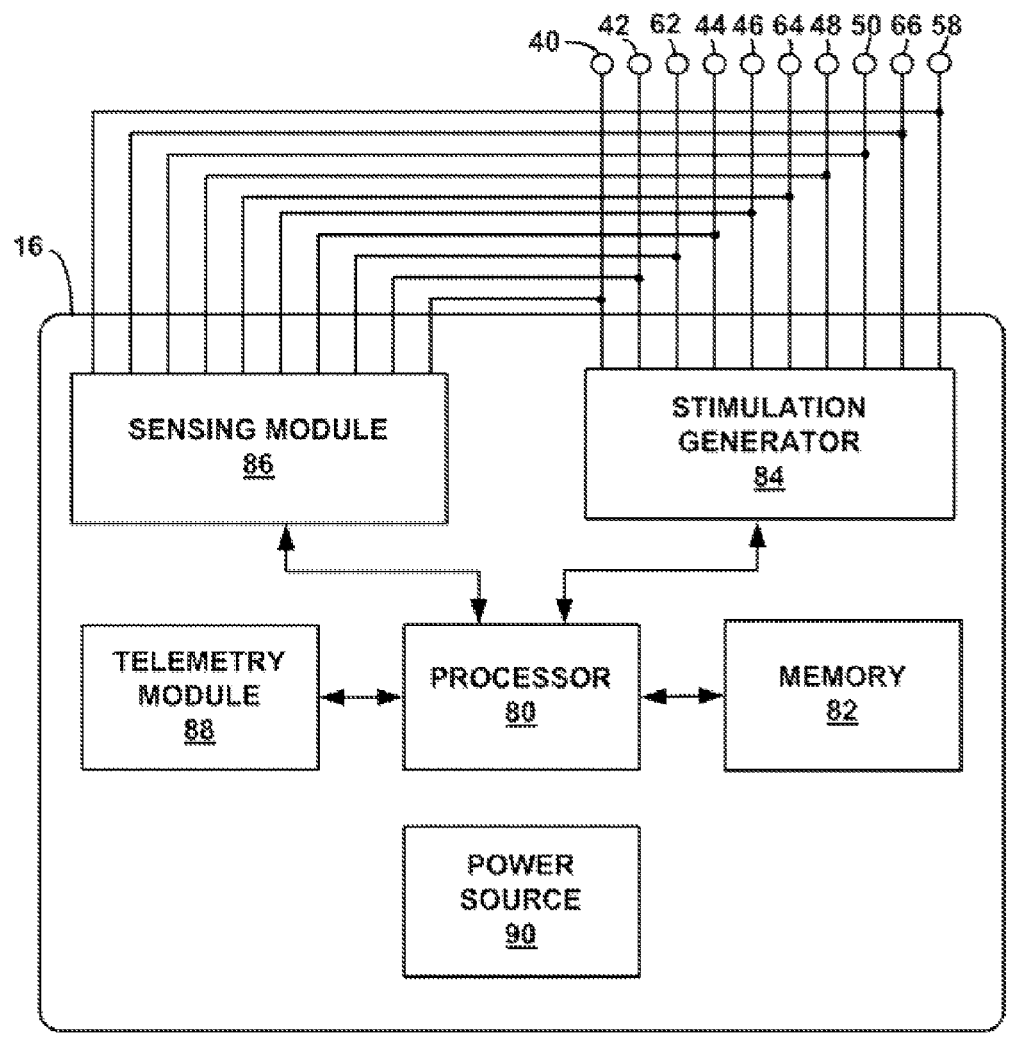
FIG. 3 is a schematic block diagram illustrating some components of an implantable medical device configured to deliver CRT to a patient.

FIG. 3 is a functional block diagram of one example configuration of IMD 16, which includes processor 80, memory 82, stimulation generator 84, sensing module 86, telemetry module 88, and power source 90. Memory 82 includes computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof. Processor 80 controls stimulation generator 84 to deliver stimulation therapy to heart 12 according to a selected one or more of therapy programs, which may be stored in memory 82. Specifically, processor 44 may control stimulation generator 84 to deliver electrical pulses with the amplitudes, pulse widths, frequency, or electrode polarities specified by the selected one or more therapy programs.

Stimulation generator 84 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of IMD 16. Stimulation generator 84 is configured to generate and deliver electrical stimulation therapy to heart 12. For example, stimulation generator 84 may deliver pacing pulses via ring electrodes 40, 44, 48 coupled to leads 18, 20, and 22, respectively, or helical electrodes 42, 46, and 50 of leads 18, 20, and 22, respectively. In some examples, stimulation generator 84 delivers pacing, cardioversion, or defibrillation stimulation in the form of electrical pulses. In other examples, stimulation generator may deliver one or more of these types of stimulation in the form of other signals, such as sine waves, square waves, or other substantially continuous time signals.

Stimulation generator 84 may include a switch module and processor 80 may use the switch module to select, e.g., via a data/address bus, which of the available electrodes are used to deliver defibrillation shocks or pacing pulses. The switch module may include a switch array, switch matrix, multiplexer, or any other type of switching device suitable to selectively couple stimulation energy to selected electrodes.

Sensing module 86 monitors signals from at least one of electrodes 40, 42, 44, 46, 48, 50, 58, 62, 64 or 66 in order to monitor electrical activity of heart 12, e.g., via electrocardiogram (ECG) signals. Sensing module 86 may also include a switch module to select which of the available electrodes are used to sense the heart activity. In some examples, processor 80 may select the electrodes that function as sense electrodes via the switch module within sensing module 86, e.g., by providing signals via a data/address bus. In some examples, sensing module 86 includes one or more sensing channels, each of which may comprises an amplifier. In response to the signals from processor 80, the switch module of within sensing module 86 may couple the outputs from the selected electrodes to one of the sensing channels.

In some examples, one channel of sensing module 86 may include an R-wave amplifier that receives signals from electrodes 40 and 42, which are used for pacing and sensing in right ventricle 28 of heart 12. Another channel may include another R-wave amplifier that receives signals from electrodes 44 and 46, which are used for pacing and sensing proximate to left ventricle 32 of heart 12. In some examples, the R-wave amplifiers may take the form of an automatic gain controlled amplifier that provides an adjustable sensing threshold as a function of the measured R-wave amplitude of the heart rhythm.

In addition, in some examples, one channel of sensing module 86 may include a P-wave amplifier that receives signals from electrodes 48 and 50, which are used for pacing and sensing in right atrium 26 of heart 12. In some examples, the P-wave amplifier may take the form of an automatic gain controlled amplifier that provides an adjustable sensing threshold as a function of the measured P-wave amplitude of the heart rhythm. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Other amplifiers may also be used. Furthermore, in some examples, one or more of the sensing channels of sensing module 86 may be selectively coupled to housing electrode 58, or elongated electrodes 62, 64, or 66, with or instead of one or more of electrodes 40, 42, 44, 46, 48 or 50, e.g., for unipolar sensing of R-waves or P-waves in any of chambers 26, 28, or 32 of heart 12.

In some examples, sensing module 86 includes a channel that comprises an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter for storage in memory 82 as an electrogram (EGM). In some examples, the storage of such EGMs in memory 82 may be under the control of a direct memory access circuit. Processor 80 may employ digital signal analysis techniques to characterize the digitized signals stored in memory 82 to detect and classify the patient's heart rhythm from the electrical signals. Processor 80 may detect and classify the heart rhythm of patient 14 by employing any of the numerous signal processing methodologies known in the art.

If IMD 16 is configured to generate and deliver pacing pulses to heart 12, processor 80 may include pacer timing and control module, which may be embodied as hardware, firmware, software, or any combination thereof. The pacer timing and control module may comprise a dedicated hardware circuit, such as an ASIC, separate from other processor 80 components, such as a microprocessor, or a software module executed by a component of processor 80, which may be a microprocessor or ASIC. The pacer timing and control module may include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber in which an electrical signal is sensed, and the third letter may indicate the chamber in which the response to sensing is provided.

Intervals defined by the pacer timing and control module within processor 80 may include atrial and ventricular pacing escape intervals, refractory periods during which sensed P-waves and R-waves are ineffective to restart timing of the escape intervals, and the pulse widths of the pacing pulses. As another example, the pace timing and control module may define a blanking period, and provide signals from sensing module 86 to blank one or more channels, e.g., amplifiers, for a period during and after delivery of electrical stimulation to heart 12. The durations of these intervals may be determined by processor 80 in response to stored data in memory 82. The pacer timing and control module of processor 80 may also determine the amplitude of the cardiac pacing pulses.

During pacing, escape interval counters within the pacer timing/control module of processor 80 may be reset upon sensing of R-waves and P-waves. Stimulation generator 84 may include pacer output circuits that are coupled, e.g., selectively by a switching module, to any combination of electrodes 40, 42, 44, 46, 48, 50, 58, 62, or 66 appropriate for delivery of a bipolar or unipolar pacing pulse to one of the chambers of heart 12. Processor 80 may reset the escape interval counters upon the generation of pacing pulses by stimulation generator 84, and thereby control the basic timing of cardiac pacing functions.

The value of the count present in the escape interval counters when reset by sensed R-waves and P-waves may be used by processor 80 to measure the durations of R-R intervals, P-P intervals, P-R intervals and R-P intervals, which are measurements that may be stored in memory 82. Processor 80 may use the count in the interval counters to detect a tachyarrhythmia event, such as ventricular fibrillation event or ventricular tachycardia event. Upon detecting a threshold number of tachyarrhythmia events, processor 80 may identify the presence of a tachyarrhythmia episode, such as a ventricular fibrillation episode, a ventricular tachycardia episode, a non-sustained tachycardia (NST) episode, or the like.

In some examples, processor 80 may operate as an interrupt driven device, and is responsive to interrupts from pacer timing and control module, where the interrupts may correspond to the occurrences of sensed P-waves and R-waves and the generation of cardiac pacing pulses. Any necessary mathematical calculations to be performed by processor 80 and any updating of the values or intervals controlled by the pacer timing and control module of processor 80 may take place following such interrupts. A portion of memory 82 may be configured as a plurality of recirculating buffers, capable of holding series of measured intervals, which may be analyzed by processor 80 in response to the occurrence of a pace or sense interrupt to determine whether the patient's heart 12 is presently exhibiting atrial or ventricular tachyarrhythmia.

In some examples, an arrhythmia detection method may include any suitable tachyarrhythmia detection algorithms. In one example, processor 80 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND GREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. and U.S. Pat. No. 5,755,736 to Gillberg et al. are incorporated herein by reference in their entireties. However, other arrhythmia detection methodologies may also be employed by processor 80 in other examples.

In the examples described herein, processor 80 may identify the presence of an atrial or ventricular tachyarrhythmia episode by detecting a series of tachyarrhythmia events (e.g., R-R or P-P intervals having a duration less than or equal to a threshold) of an average rate indicative of tachyarrhythmia or an unbroken series of short R-R or P-P intervals. The thresholds for determining the R-R or P-P interval that indicates a tachyarrhythmia event may be stored within memory 82 of IMD 16. In addition, the number of tachyarrhythmia events that are detected to confirm the presence of a tachyarrhythmia episode may be stored as a number of intervals to detect (NID) threshold value in memory 82. In some examples, processor 80 may also identify the presence of the tachyarrhythmia episode by detecting a variable coupling interval between the R-waves of the heart signal. For example, if the interval between successive tachyarrhythmia events varies by a particular percentage or the differences between the coupling intervals are higher than a given threshold over a predetermined number of successive cycles, processor 80 may determine that the tachyarrhythmia is present.

If processor 80 detects an atrial or ventricular tachyarrhythmia based on signals from sensing module 86, and an anti-tachyarrhythmia pacing regimen is desired, timing intervals for controlling the generation of anti-tachyarrhythmia pacing therapies by stimulation generator 84 may be loaded by processor 80 into the pacer timing and control module to control the operation of the escape interval counters therein and to define refractory periods during which detection of R-waves and P-waves is ineffective to restart the escape interval counters.

If IMD 16 is configured to generate and deliver defibrillation shocks to heart 12, stimulation generator 84 may include a high voltage charge circuit and a high voltage output circuit. In the event that generation of a cardioversion or defibrillation shock is required, processor 80 may employ the escape interval counter to control timing of such cardioversion and defibrillation shocks, as well as associated refractory periods. In response to the detection of atrial or ventricular fibrillation or tachyarrhythmia requiring a cardioversion pulse, processor 80 may activate a cardioversion/defibrillation control module, which may, like pacer timing and control module, be a hardware component of processor 80 and/or a firmware or software module executed by one or more hardware components of processor 80. The cardioversion/defibrillation control module may initiate charging of the high voltage capacitors of the high voltage charge circuit of stimulation generator 84 under control of a high voltage charging control line.

Processor 80 may monitor the voltage on the high voltage capacitor, e.g., via a voltage charging and potential (VCAP) line. In response to the voltage on the high voltage capacitor reaching a predetermined value set by processor 80, processor 80 may generate a logic signal that terminates charging. Thereafter, timing of the delivery of the defibrillation or cardioversion pulse by stimulation generator 84 is controlled by the cardioversion/defibrillation control module of processor 80. Following delivery of the fibrillation or tachycardia therapy, processor 80 may return stimulation generator 84 to a cardiac pacing function and await the next successive interrupt due to pacing or the occurrence of a sensed atrial or ventricular depolarization.

Stimulation generator 84 may deliver cardioversion or defibrillation shocks with the aid of an output circuit that determines whether a monophasic or biphasic pulse is delivered, whether housing electrode 58 serves as cathode or anode, and which electrodes are involved in delivery of the cardioversion or defibrillation shocks. Such functionality may be provided by one or more switches or a switching module of stimulation generator 84.

Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and the control signals for the telemetry circuit within telemetry module 88, e.g., via an address/data bus. In some examples, telemetry module 88 may provide received data to processor 80 via a multiplexer.

In some examples, processor 80 may transmit atrial and ventricular heart signals (e.g., electrocardiogram signals) produced by atrial and ventricular sense amp circuits within sensing module 86 to programmer 24. Programmer 24 may interrogate IMD 16 to receive the heart signals. Processor 80 may store heart signals within memory 82, and retrieve stored heart signals from memory 82. Processor 80 may also generate and store marker codes indicative of different cardiac episodes that sensing module 86 detects, and transmit the marker codes to programmer 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety.

The various components of IMD 16 are coupled to power source 90, which may include a rechargeable or non-rechargeable battery. A non-rechargeable battery may be selected to last for several years, while a rechargeable battery may be inductively charged from an external device, e.g., on a daily or weekly basis.

Figure 4:
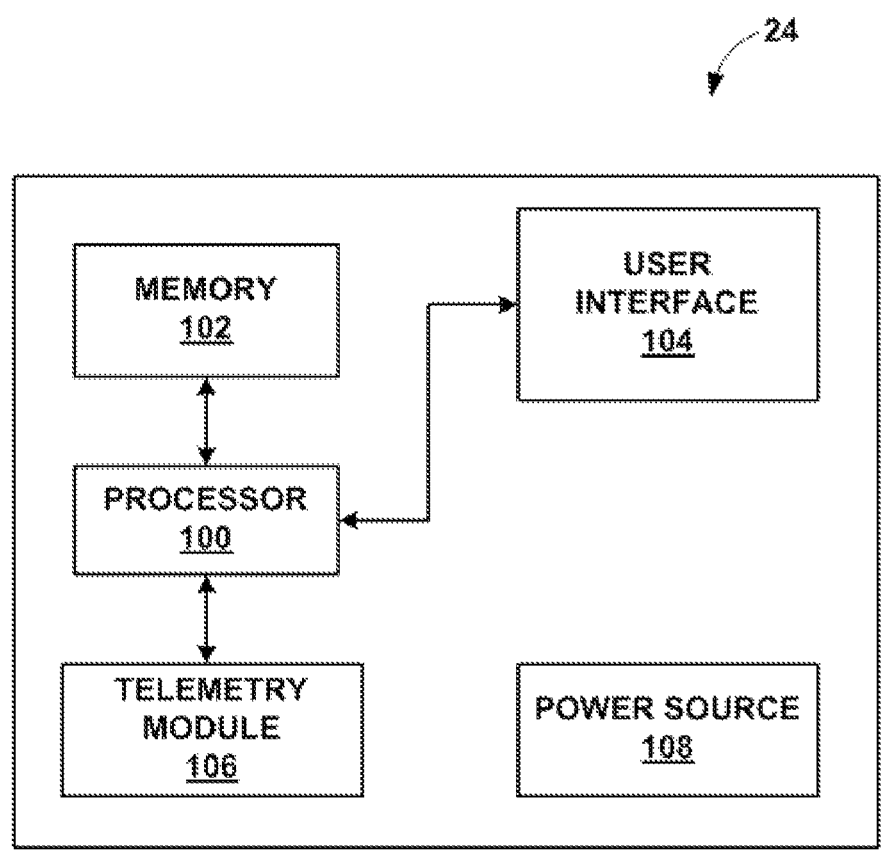
FIG. 4 is a schematic block diagram illustrating some components of a programmer device configured to communicate with an implantable medical device.

FIG. 4 is block diagram of an example programmer 24. As shown in FIG. 4, programmer 24 includes processor 100, memory 102, user interface 104, telemetry module 106, and power source 108. Programmer 24 may be a dedicated hardware device with dedicated software for programming of IMD 16. Alternatively, programmer 24 may be an off-the-shelf computing device running an application that enables programmer 24 to program IMD 16.

A user may use programmer 24 to select therapy programs (e.g., sets of stimulation parameters), generate new therapy programs, modify therapy programs through individual or global adjustments or transmit the new programs to a medical device, such as IMD 16 (FIG. 1). The clinician may interact with programmer 24 via user interface 104, which may include display to present graphical user interface to a user, and a keypad or another mechanism for receiving input from a user.

Processor 100 can take the form one or more microprocessors, DSPs, ASICs, FPGAs, programmable logic circuitry, or the like, and the functions attributed to processor 102 herein may be embodied as hardware, firmware, software or any combination thereof. Memory 102 may store instructions that cause processor 100 to provide the functionality ascribed to programmer 24 herein, and information used by processor 100 to provide the functionality ascribed to programmer 24 herein. Memory 102 may include any fixed or removable magnetic, optical, or electrical media, such as RAM, ROM, CD-ROM, hard or floppy magnetic disks, EEPROM, or the like. Memory 102 may also include a removable memory portion that may be used to provide memory updates or increases in memory capacities. A removable memory may also allow patient data to be easily transferred to another computing device, or to be removed before programmer 24 is used to program therapy for another patient. Memory 102 may also store information that controls therapy delivery by IMD 16, such as stimulation parameter values.

Programmer 24 may communicate wirelessly with IMD 16, such as using RF communication or proximal inductive interaction. This wireless communication is possible through the use of telemetry module 102, which may be coupled to an internal antenna or an external antenna. An external antenna that is coupled to programmer 24 may correspond to the programming head that may be placed over heart 12, as described above with reference to FIG. 1. Telemetry module 102 may be similar to telemetry module 88 of IMD 16 (FIG. 3).

Telemetry module 102 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection.

Power source 108 delivers operating power to the components of programmer 24. Power source 108 may include a battery and a power generation circuit to produce the operating power. In some embodiments, the battery may be rechargeable to allow extended operation. Recharging may be accomplished by electrically coupling power source 108 to a cradle or plug that is connected to an alternating current (AC) outlet. In addition or alternatively, recharging may be accomplished through proximal inductive interaction between an external charger and an inductive charging coil within programmer 24. In other embodiments, traditional batteries (e.g., nickel cadmium or lithium ion batteries) may be used. In addition, programmer 24 may be directly coupled to an alternating current outlet to power programmer 24. Power source 104 may include circuitry to monitor power remaining within a battery. In this manner, user interface 104 may provide a current battery level indicator or low battery level indicator when the battery needs to be replaced or recharged. In some cases, power source 108 may be capable of estimating the remaining time of operation using the current battery.

Referring again to FIG. 3, processor 80 of IMD 16 may detect a tachyarrhythmia episode, such as a ventricular fibrillation, ventricular tachycardia, fast ventricular tachyarrhythmia episode, a NST episode, or the like, based on electrocardiographic activity of heart 12 that is monitored via sensing module 86. For example, sensing module 86, with the aid of at least some of the electrodes 40, 42, 44, 46, 48, 50, 58, 62, 64, and 66 (shown in FIGS. 1-2), may generate an electrocardiogram (ECG) or electrogram (EGM) signal that indicates the electrocardiographic activity. Alternatively, sensing module 86 may be coupled to sense electrodes that are separate from the stimulation electrodes that deliver electrical stimulation to heart 12 (shown in FIGS. 1-2), and may be coupled to one or more different leads than leads 18, 20, 22 (shown in FIGS. 1-2). The ECG signal may be indicative of the depolarization of heart 12.

For example, as previously described, in some examples, processor 80 may identify the presence of a tachyarrhythmia episode by detecting a threshold number of tachyarrhythmia events (e.g., R-R or P-P intervals having a duration less than or equal to a threshold). In some examples, processor 80 may also identify the presence of the tachyarrhythmia episode by detecting a variable coupling interval between the R-waves of the heart signal.

Figure 5:
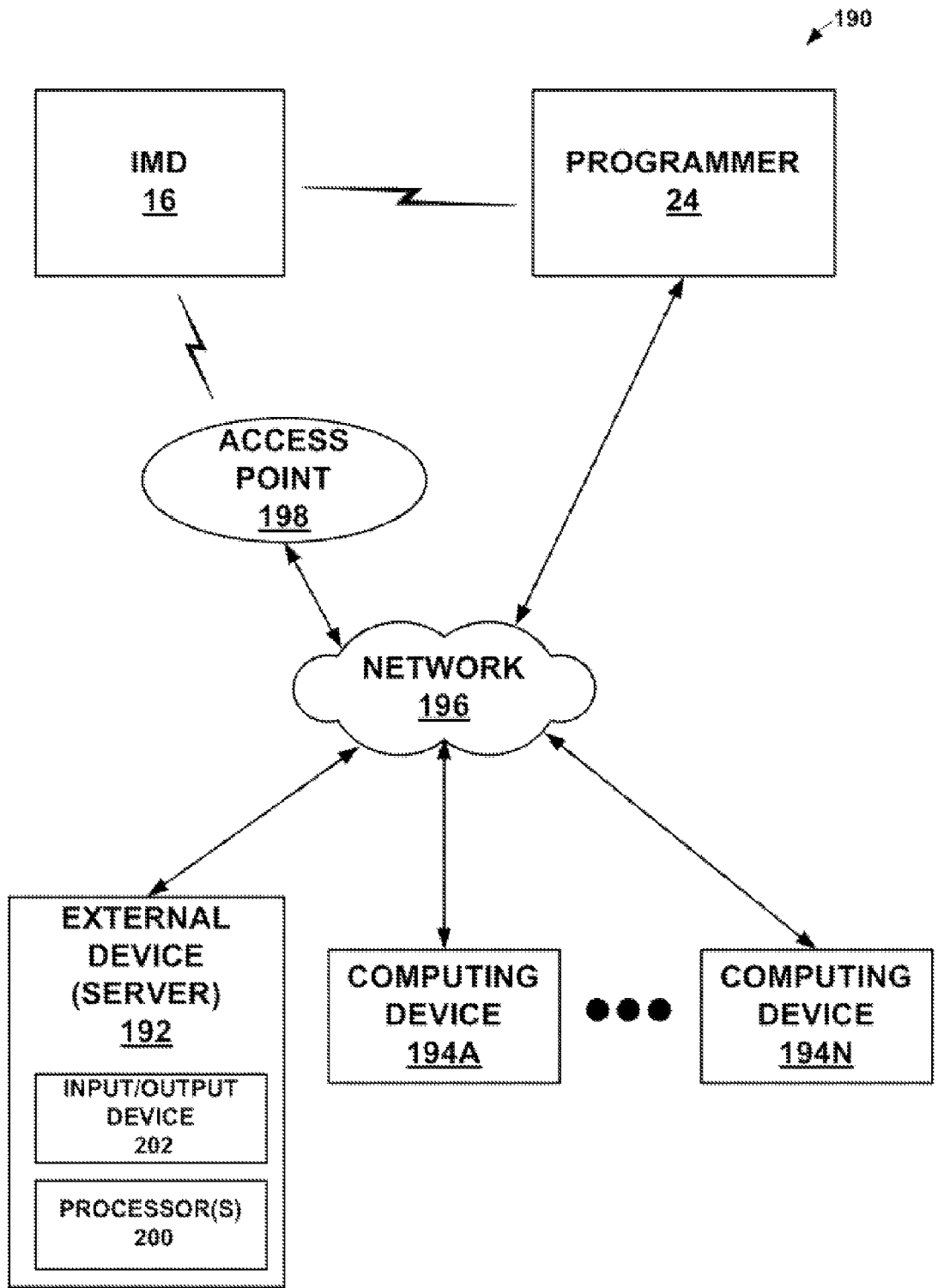
FIG. 5 is a schematic block diagram illustrating a system that includes an external device, such as a server, and one or more computing devices that are coupled to an implantable medical device and programmer via a network.

FIG. 5 is a block diagram illustrating a system 190 that includes an external device 132, such as a server, and one or more computing devices 194A-194N that are coupled to IMD 16 and programmer 24 shown in FIG. 1 via a network 196, according to one embodiment. In this embodiment, IMD 16 uses its telemetry module 88 to communicate with programmer 24 via a first wireless connection, and to communicate with an access point 198 via a second wireless connection. In the example of FIG. 5, access point 198, programmer 24, external device 192, and computing devices 194A-194N are interconnected, and able to communicate with each other, through network 196. In some cases, one or more of access point 198, programmer 24, external device 192, and computing devices 194A-194N may be coupled to network 196 through one or more wireless connections. IMD 16, programmer 24, external device 192, and computing devices 194A-194N may each comprise one or more processors, such as one or more microprocessors, DSPs, ASICs, FPGAs, programmable logic circuitry, or the like, that may perform various functions and operations, such as those described herein.

Access point 198 may comprise a device that connects to network 196 via any of a variety of connections, such as telephone dial-up, digital subscriber line (DSL), or cable modem connections. In other examples, access point 198 may be coupled to network 130 through different forms of connections, including wired or wireless connections. In some examples, access point 198 may communicate with programmer 24 and/or IMD 16. Access point 198 may be co-located with patient 14 (e.g., within the same room or within the same site as patient 14) or may be remotely located from patient 14. For example, access point 198 may be a home monitor that is located in the patient's home or is portable for carrying with patient 14.

During operation, IMD 16 may collect, measure, and store various forms of diagnostic data. In certain cases, IMD 16 may directly analyze collected diagnostic data and generate any corresponding reports or alerts. In some cases, however, IMD 16 may send diagnostic data to programmer 24, access point 198, and/or external device 192, either wirelessly or via access point 198 and network 196, for remote processing and analysis.

In some cases, IMD 16 and/or programmer 24 may combine all of the diagnostic data into a single displayable lead integrity report, which may be displayed on programmer 24. The lead integrity report contains diagnostic information concerning one or more electrode leads that are coupled to IMD 16, such as leads 18, 20, or 22. A clinician or other trained professional may review and/or annotate the lead integrity report, and possibly identify any lead-related conditions.

In another example, IMD 16 may provide external device 192 with collected diagnostic data via access point 198 and network 196. External device 192 includes one or more processors 200. In some cases, external device 192 may request such data, and in some cases, IMD 16 may automatically or periodically provide such data to external device 192. Upon receipt of the diagnostic data via input/output device 202, external device 192 is capable of analyzing the data and generating reports or alerts upon determination that there may be a possible condition with one or more of leads 18, 20, and 22. For example, one or more of leads 18, 20, and 22 may experience a condition related to a lead fracture or an insulation breach.

In one embodiment, external device 192 may combine the diagnostic data into a lead integrity report. One or more of computing devices 194A-194N may access the report through network 196 and display the report to users of computing devices 194A-194N. In some cases, external device 192 may automatically send the report via input/output device 202 to one or more of computing devices 194A-194N as an alert, such as an audio or visual alert. In some cases, external device 192 may send the report to another device, such as programmer 24, either automatically or upon request. In some cases, external device 192 may display the report to a user via input/output device 196.

In one embodiment, external device 192 may comprise a secure storage site for diagnostic information that has been collected from IMD 16 and/or programmer 24. In this embodiment, network 196 may comprise an Internet network, and trained professionals, such as clinicians, may use computing devices 194A-194N to securely access stored diagnostic data on external device 192. For example, the trained professionals may need to enter usernames and passwords to access the stored information on external device 192. In one embodiment, external device 192 may be a CareLink server provided by Medtronic, Inc., of Minneapolis, Minn.

2. Methods and Algorithms

As described above, selection of an appropriate vein for purposes of left ventricular lead placement may be important for improving the efficiency or rate of response for CRT. As described in the Examples below, it has been found that those coronary sinus veins with a high degree of electrical dispersion with regard to local myocardial activation time may be good candidates for left ventricular lead placement for CRT. More particularly, it has been found that left ventricular coronary sinus electrical dispersion during or following right ventricular pacing is predictive of effectiveness for biventricular CRT. It is also suggested that left ventricular coronary sinus electrical dispersion associated with an intrinsic right ventricular contraction may be predictive of effective left ventricular CRT.

Figure 6:
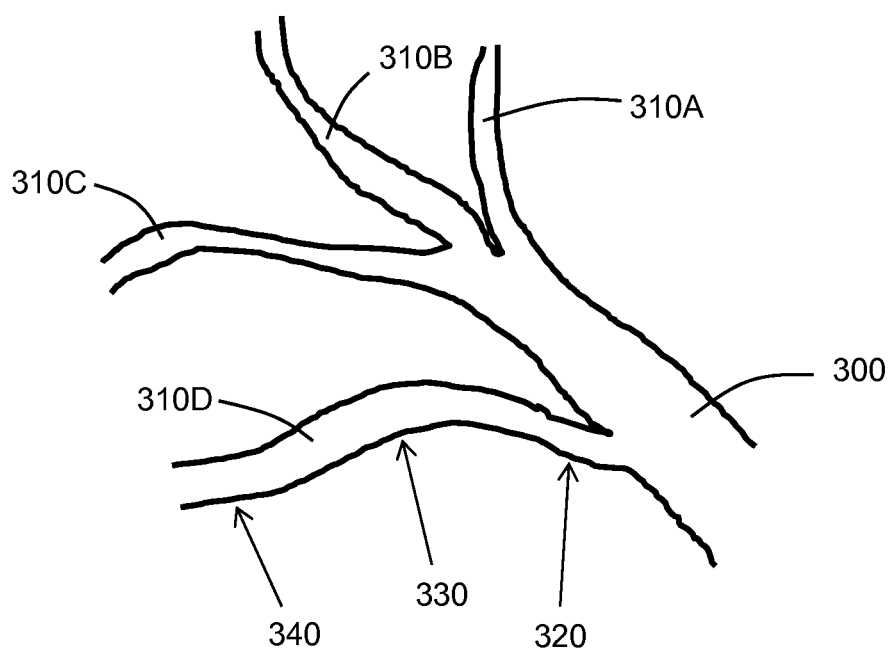
FIG. 6 is a schematic drawing illustrating a coronary sinus and associated veins.

To determine electrical dispersion of a coronary sinus vein, electrical activity in or along the vein at a plurality of locations is determined. As used herein, a "coronary sinus vein" is a vein or branch or sub-branch of a vein extending from the coronary sinus. For example and with reference to FIG. 6, a schematic drawing of a coronary sinus 300 and associated veins 310A-D are illustrated. Local electrical activity or myocardial activation may be detected at more than one location of a vein 310, such as at a relatively distal 340 location of vein 310D, a relatively mid 330 location of vein 310D, and a relatively proximal 320 location of vein 310D, to determine electrical dispersion of the vein 310D.

The local activity at the plurality of locations 320, 330, 340 of vein 301D may be measured in any suitable manner. For example, a lead having an electrode may be advanced to one of the locations (e.g., 320) and electrical activity measured (e.g., through sensing circuitry of a device coupled the lead), advanced to another of the locations (e.g., 330) and electrical activity measured or monitored, and advanced to yet another of the locations (e.g., 340) and electrical activity measured and monitored. Timing of an event of electrical activity measured or monitored at each location (e.g., myocardial activation) may be compared to a timing of a fiducial of electrical activity of the heart for purposes of determining electrical dispersion.

In embodiments, a lead having a plurality of electrodes is advanced through vein (e.g. vein 310D) such that an electrode is located at position 320, another electrode is located at position 330, and another electrode is located at position 340. Local electrical activity at each position 320, 330, 340 may then be measured or monitored by the electrodes of the lead.

In embodiments, local electrical activity or myocardial activation times are determined non-invasively (e.g. as described above). A map of the activation times may be overlaid on an image of coronary veins of the left ventricle, or vice versa (which will be equivalent for the purposes of the present disclosure). Electrical dispersions (ED) along various coronary sinus veins overlaying the left ventricle may be determined to identify suitable target veins for left ventricle lead placement for CRT (e.g., a vein meeting or exceeding a predetermined ED threshold or having the highest degree of ED).

Figure 7:
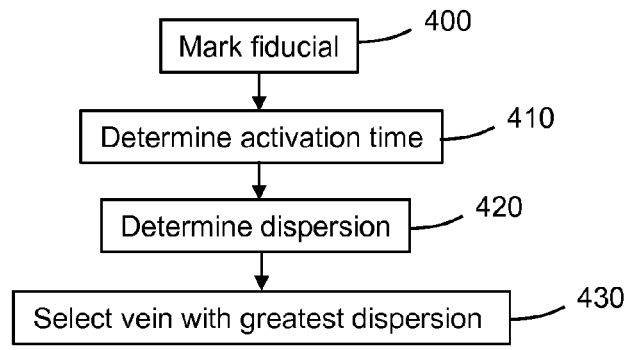
FIGS. 7-13 are flow diagrams illustrating processes for selecting a target vein for left ventricular lead placement for CRT according to various embodiments described herein.

Referring now to FIGS. 7-13, overviews of methods or algorithms that may be employed for purposes of identifying a candidate vein for left ventricular lead placement for CRT are shown. With reference to FIG. 7, a process may include marking timing of a fiducial of electrical activity of the heart (400), determining myocardial activation times at a plurality of locations of a coronary vein (410), and determining electrical dispersion of the vein (420). This process may be repeated for several veins, and the vein with the highest electrical dispersion may be selected as the target vein for CRT (430).

Figure 8:
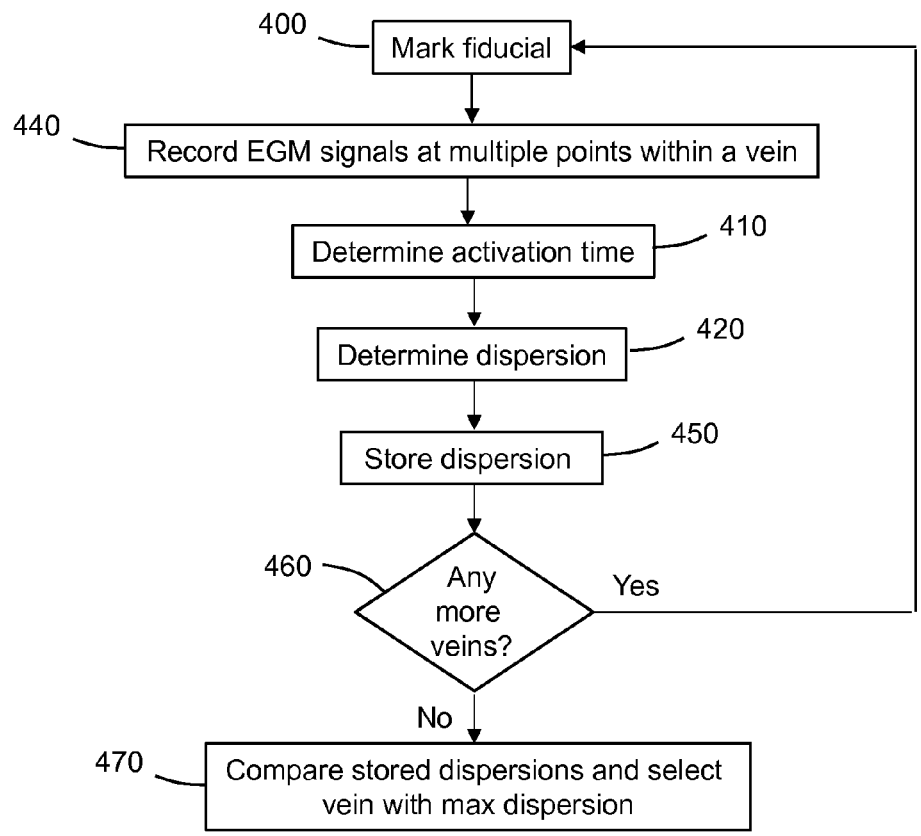

FIG. 8 illustrates an embodiment of the process of FIG. 7 in greater detail. In the process of FIG. 8, the timing of a fiducial of electrical activity of the heart is marked (400); e.g., by time stamping and storing in memory, and electrograms are recorded at a plurality of locations within a coronary vein overlaying the left ventricle (440), which may be done with a multiple electrode lead or a lead with an electrode that is advanced to the plurality of locations in the vein. Myocardial activation times may be determined relative to the timing of the fiducial (410), and electrical dispersion may be determined from the activation times (420). The electrical dispersion for vein may be stored in memory (450) for later recall and comparison. In some embodiments (not shown), data regarding electrical dispersion of a vein is displayed for a user to view (e.g. on a programmer device, or the like). A determination is then made as to whether there are any additional veins for which electrical dispersion may be made (460). Such a determination may be made by a health care professional; e.g. a physician that is positioning the lead within the vein. In embodiments, the system or device calculating the activation times or dispersion may receive input as to whether additional veins are to be tested. If there are more veins, the process is repeated until dispersion data is collected for all of the veins to be sampled. Once electrical dispersion data has been stored for all of the veins to be sampled, the stored dispersion data is compared and the vein with the maximum electrical dispersion may be selected (470).

Figure 9:
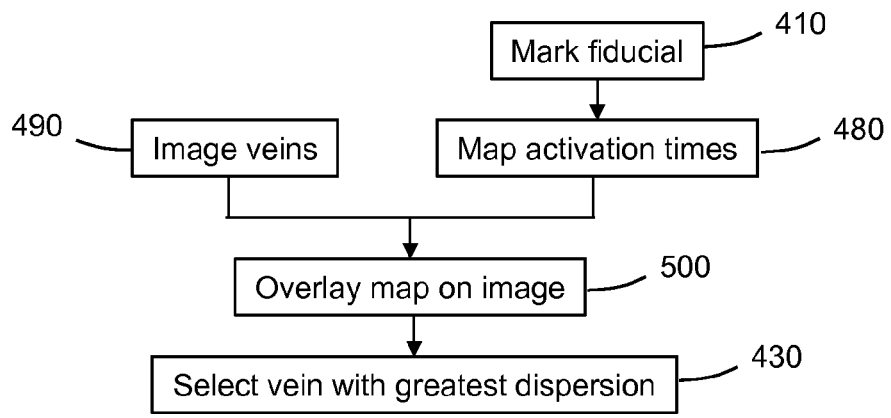

FIG. 9 illustrates an alternative embodiment of the process of FIG. 7 in greater detail. In the process of FIG. 9, the timing of a fiducial is marked (410) and myocardial activation times of the heart or left ventricle are mapped noninvasively (480). An image of coronary veins overlaying the left ventricle is obtained (490); e.g. via fluoro-imaging, MRI or the like. The map of activation times is overlaid on the image of the coronary veins (500). This step is preferably done figuratively by software, but may be displayed for a user to view. Based on the imaged veins and activation time map, electrical dispersion of various veins may be determined. The vein with the greatest dispersion may be selected (430).

It will be understood that FIGS. 8-9 illustrate only some examples of ways in which the process of FIG. 7 may be carried out and that other ways, methods, or algorithms are contemplated herein.

Figure 10:
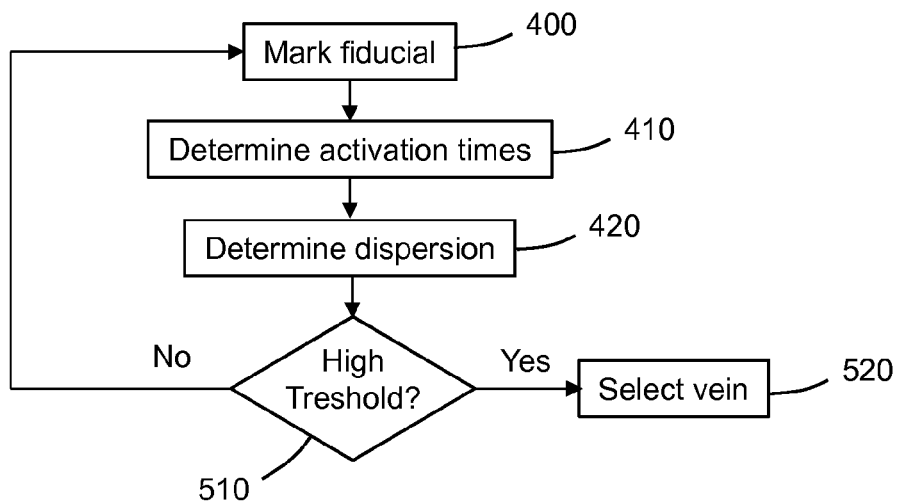

Referring now to FIG. 10, an overview of an alternative of supplemental process for identifying a candidate vein for left ventricular lead placement for CRT is shown. The process includes marking timing of a fiducial of electrical activity of the heart (400), determining myocardial activation times at a plurality of locations of a coronary vein (410), and determining electrical dispersion of the vein (420). A determination is then made as to whether the electrical dispersion of the vein meets or exceeds a threshold that is highly predictive of a suitable vein for left ventricular lead placement for CRT (510). If the electrical dispersion meets or exceeds the threshold, the vein is selected (520). If the vein does not meet or exceed the highly predictive threshold, process may be repeated for another vein.

Figure 11:
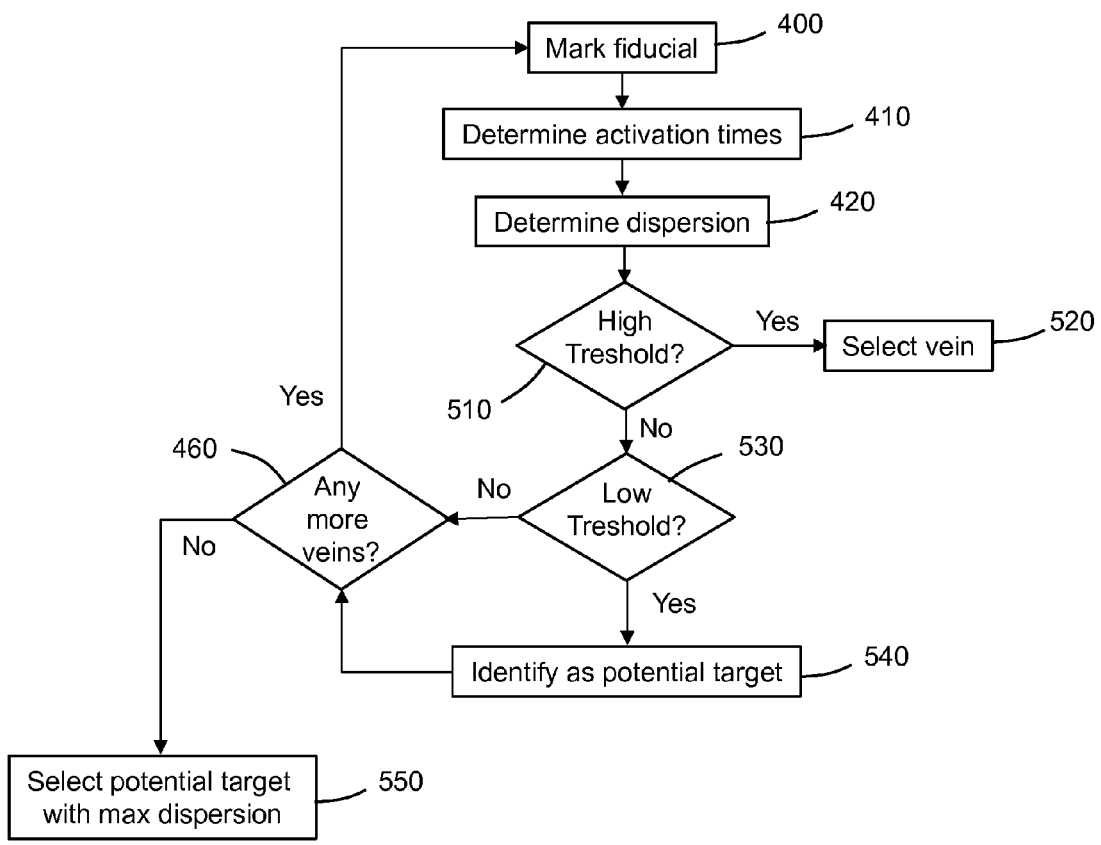

FIG. 11 depicts a process similar to FIG. 10. As with FIG. 10, the process of FIG. 11 includes marking timing of a fiducial of electrical activity of the heart (400), determining myocardial activation times at a plurality of locations in a vein relative to the fiducial (410), determining electrical dispersion of the vein based on the activation times (420), determining whether the highly predictive threshold is met or exceeded (510) and selecting the vein if the highly predictive threshold is met or exceeded (520). If the highly predictive threshold is not met, the process of FIG. 11 further includes determining whether a lower threshold of electrical dispersion for the vein is met (530). Preferably, the lower threshold is a threshold wherein some veins (e.g., 25% or more, 50% or more, or 75% or more) meeting or exceeding the threshold (but not meeting or exceeding the highly predictive threshold) produce good results when used for left ventricular lead placement for CRT. If the lower threshold is met, the vein is identified as a potential target (540) for lead placement. For example, data regarding the electrical dispersion of the vein may be saved into memory for later recall or comparison. If the lower threshold is not met or exceeded, a determination is made as to whether any more veins are to be sampled (460). If more veins are to be sampled the process is repeated until a vein meeting or exceeding the high threshold is identified or until no more veins are to be sampled. If no more veins are to be sampled and none have met or exceeded the high threshold, electrical dispersion of the identified potential target veins are compared (e.g. read from memory) and the vein with the highest dispersion is selected (550).

It will be understood that the process depicted in FIG. 11 may employ a noninvasive process (e.g., as described above with regard to FIG. 9) or a process in which activation times are monitored via electrodes in a vein (e.g. as described above with regard to FIG. 8).

Figure 12:
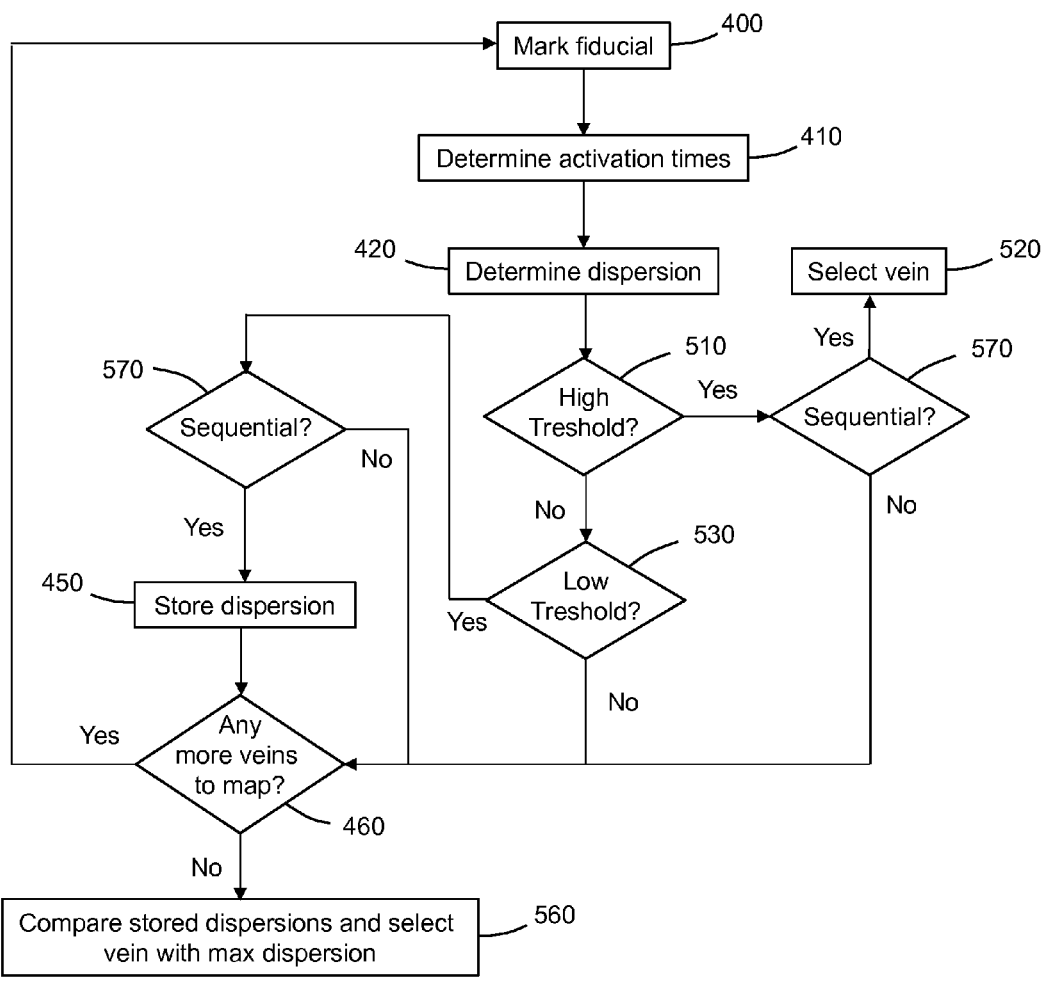

FIG. 12 illustrates a process similar to the process described in FIG. 11, with like numbers referring to like or similar steps, but includes steps related to the sequence of activation times in or along a coronary vein. As described below in the Examples, the sequence of activation may be a contributing or determinative factor in determining whether a vein will serve as a suitable vein for left ventricular lead placement for CRT. As shown in the Examples, veins in which myocardial activation is sequential from distal portions to proximal portions serve as suitable veins for left ventricular pacing, while those which do not exhibit such sequential activation may not serve as suitable veins for left ventricular pacing. As indicated in FIG. 12, automatic selection of a vein (520) occurs if the electrical dispersion of the vein meets or exceeds the high threshold (510) and sequential activation (distal to proximal) is observed (570). If sequential activation is not observed, even when the high threshold is met or exceeded, a determination is made as to whether there are any more veins to sample or map (460) rather than selecting the vein. Similarly, data regarding veins that meet or exceed the low threshold (530) but do not meet the high threshold (510) is stored (450) only when sequential activation is observed (570). If no veins are identified that meet or exceed the high electrical dispersion threshold and in which sequential activation is observed and if no more veins are to be sampled or mapped, the stored data regarding veins meeting or exceeding the low threshold (but not the high threshold) and in which sequential activation occurred is compared and the vein with the largest electrical dispersion is selected.

As with the process of FIG. 11, it will be understood that the process depicted in FIG. 12 may employ a noninvasive process (e.g., as described above with regard to FIG. 9) or a process in which activation times are monitored via electrodes in a vein (e.g. as described above with regard to FIG. 8).

Figure 13:
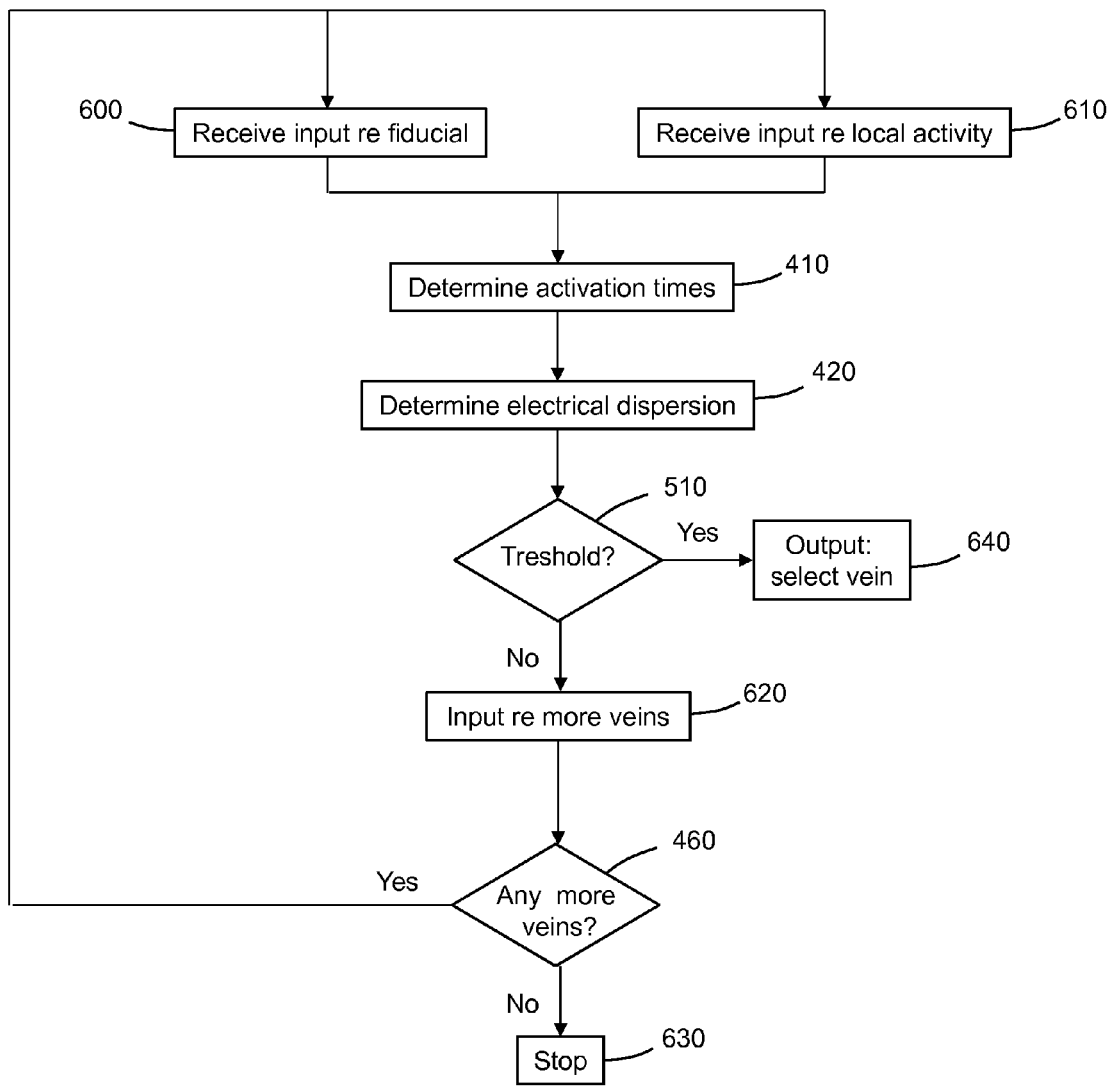

Referring now to FIG. 13, a method carried out by a device or system is illustrated. The device or system receives input regarding the timing of a fiducial (600); e.g. via a sensing circuit operably coupled to an electrode, and receives input regarding local electrical activity (610) at a plurality of locations in or along a vein; e.g. via a sensing circuit operably coupled to an electrode. Activation times are determined (410) based on the input regarding the fiducial and the local electrical activity, and electrical dispersion for the vein is determined (420). A determination is made as to whether the electrical dispersion of the vein is met or exceeded (510). If the threshold is met or exceeded, the device or system outputs data indicating that the vein may be selected (640). In embodiments, the output data includes the calculated electrical dispersion value. If the threshold is not met or exceeded, the device or system may receive input regarding whether additional veins are to be sampled or mapped (620). The device or system may prompt a user to enter input following a determination that the threshold has not been met or exceeded as depicted in FIG. 13 or may receive the input earlier in the process (not shown, e.g. by prompting a user to input the number of veins to be sampled or mapped upfront). If more veins are to be mapped or sampled (460), the process is repeated until a vein meeting or exceeding the electrical dispersion threshold is identified or until no more veins are to be sampled or mapped, and the process is stopped (630).

It will be understood that any of the methods depicted and described with regard to FIGS. 7-12 may be modified in a manner as described with regard to FIG. 13 to be carried out entirely by a device or system (as opposed to having one more steps carried out by a user, such as a physician).

The techniques described in this disclosure, including those attributed to IMD, programmer device, or the like, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

A number of embodiments of methods, devices, and systems are described herein. A summary of selected aspects of methods, devices and systems described herein is provided below.

A first aspect is a method for selecting a target vein for left ventricular lead placement for cardiac resynchronization therapy. The method comprises (a) marking timing of a fiducial of electrical activity of the heart; (b) determining a myocardial activation time, relative to the timing of the fiducial, at each of a plurality of locations in or along a first coronary vein overlying a left ventricle; (c) determining an electrical dispersion for the first coronary vein, wherein determining the electrical dispersion comprises calculating the difference between (i) the activation time at the location that had the latest activation time of the plurality of locations and (ii) the activation time at the location that had the earliest activation time of the plurality of locations; (d) determining whether the magnitude of the electrical dispersion for the first vein meets or exceeds a predetermined high threshold; and (e) identifying the first vein as the target vein for left ventricular lead placement if the electrical dispersion for the vein meets or exceeds the predetermined high threshold.

A $2^{nd}$ aspect is a method of the first aspect, wherein marking timing of the fiducial of electrical activity of the heart comprises marking the timing electrical activity selected from the group consisting of a fiducial of pacing or a fiducial of an intrinsic sinus rhythm.

A $3^{rd}$ aspect is a method of the $1^{st}$ aspect, wherein marking timing of the fiducial of electrical activity of the heart comprises marking the timing of electrical activity selected from the group consisting of pacing of a right ventricle, a peak of an R-wave, and onset of QRS.

A $4^{th}$ aspect is a method of any of aspects 1-3, wherein determining the myocardial activation time, relative to the timing of the fiducial, at each of the plurality of locations in or along the first coronary vein comprises correlating a map of activation times across the heart to an image of the heart in which the first coronary vein is detectable, and identifying the activation time at each of the plurality of locations in or along the first coronary vein.

A $5^{th}$ aspect is a method of any of aspects 1-3, wherein determining the myocardial activation time, relative to the timing of the fiducial, at each of the plurality of locations in or along the first coronary vein comprises sensing activation via a plurality of electrodes of a lead, wherein at least one electrode of the lead is positioned at each of the plurality of locations in or along the first coronary vein.

A $6^{th}$ aspect is a method of any of aspects 1-3, wherein determining the myocardial activation time, relative to the timing of the fiducial, at each of the plurality of locations in or along the first coronary vein comprises: (a) sensing activation, via an electrode of a lead, at one of the plurality of locations in or along the first coronary vein; (b) moving the electrode to another of the plurality of locations in or along the first coronary vein and sensing activation via the electrode at the other location; and (c) repeating step (b), if necessary, until activation has been sensed at each of the plurality of locations in or along the first coronary vein.

A $7^{th}$ aspect is a method of any of aspects 1-6, wherein, if the electrical dispersion for the first vein is determined to not meet or exceed the predetermined threshold, the method further comprises: (a) marking timing of the fiducial of electrical activity of the heart; (b) determining a myocardial activation time, relative to the timing of the fiducial, at each of a plurality of locations in or along a second coronary vein overlying the left ventricle; (c) determining an electrical dispersion for the second coronary vein by calculating the difference between (i) the activation time at the location that had the latest activation time of the plurality of locations and (ii) the activation time at the location that had the earliest activation time of the plurality of locations; (d) determining whether the magnitude of the electrical dispersion for the second vein meets or exceeds the predetermined high threshold; and (e) identifying the second vein as the target vein for left ventricular lead placement if the electrical dispersion for the vein meets or exceeds the predetermined high threshold.

An $8^{th}$ aspect is a method of any of aspects 1-7, further comprising determining whether the magnitude of the electrical dispersion for the first vein meets or exceeds a predetermined mid threshold; and identifying the first vein as a possible target vein for left ventricular lead placement if the electrical dispersion for the vein meets or exceeds the predetermined mid threshold, but not the predetermined high threshold.

A $9^{th}$ aspect is a method of any of aspects 1-8, further comprising determining whether the magnitude of the electrical dispersion for the first vein meets or exceeds a predetermined low threshold; and excluding the first vein as the target vein for left ventricular lead placement if the electrical dispersion for the vein does not meet or exceed the predetermined low threshold.

A $10^{th}$ aspect is a method of any of aspects 1-9, wherein the plurality of locations in or along the first vein comprises three or more locations.

An $11^{th}$ aspect is a method carried out by a device configured to assist in selecting a target vein for left ventricular lead placement for cardiac resynchronization therapy, comprising: (a) receiving input regarding timing of a fiducial of electrical activity of the heart; (b) receiving input regarding local electrical activity at a plurality of locations in or along a first coronary vein overlaying a left ventricle; (c) determining a myocardial activation time, relative to the timing of the fiducial, of each of the plurality of locations in or along the first coronary vein; (d) determining an electrical dispersion for the first coronary vein, wherein determining the electrical dispersion comprises calculating the difference between (i) the activation time at the location that had the latest activation time of the plurality of locations and (ii) the activation time at the location that had the earliest activation time of the plurality of locations; and (e) determining whether the magnitude of the electrical dispersion for the first vein meets or exceeds a predetermined threshold.

A $12^{th}$ aspect is a method of the $11^{th}$ aspect, further comprising outputting data indicating whether the threshold was met or exceeded.

A $13^{th}$ aspect is a method of the $12^{th}$ aspect, wherein outputting the data comprises outputting a value of the magnitude of the electrical dispersion of the first vein.

A $14^{th}$ aspect is a computer readable medium for a system configured to identify a target vein for left ventricular lead placement for cardiac resynchronization therapy, the computer readable medium comprising instructions that, when implemented, cause the system to: (a) mark timing of a fiducial of electrical activity of the heart; (b) determine a myocardial activation time, relative to the timing of the fiducial, at each of a plurality of locations in or along a first coronary vein overlying a left ventricle; (c) determine an electrical dispersion for the first coronary vein by calculating the difference between (i) the activation time at the location that had the latest activation time of the plurality of locations and (ii) the activation time at the location that had the earliest activation time of the plurality of locations; (d) determine whether the magnitude of the electrical dispersion for the first vein meets or exceeds a predetermined threshold; and (e) indicate the first vein as the target vein for left ventricular lead placement if the electrical dispersion for the first vein meets or exceeds a predetermined threshold.

A 15$^{th}$ aspect is a system comprising: (a) the computer readable medium of the 14$^{th}$ aspect, (b) electronics capable of executing the instructions of the computer readable medium; (c) one or more electrodes configured to sense electrical data from each of the plurality of locations in or along a first coronary vein overlying the left ventricle and to provide the electronics with the sensed data; and (d) one or more electrodes configured to sense a fiducial of electrical activity of the heart and configured to provide data regarding the fiducial to the electronics.

A 16$^{th}$ aspect is a system comprising: (a) the computer readable medium of the 14$^{th}$ aspect, (b) electronics capable of executing the instructions of the computer readable medium; (c) one or more electrodes configured to sense electrical data from each of the plurality of locations in or along a first coronary vein overlying the left ventricle and to provide the electronics with the sensed data; and (d) a memory configured to record timing of a pacing event of the heart and to provide data regarding the timing of the pacing event to the electronics, wherein the timing of the pacing event is the timing of the fiducial.

A 17$^{th}$ aspect is a device comprising: (a) the computer readable medium the 14$^{th}$ aspect, (b) a processor capable of executing the instructions of the computer readable medium; (c) one or more local sensing circuits operably coupled to the processor, wherein the one or more sensing circuits are configured to receive input from one or more electrodes configured to sense electrical data from each of the plurality of locations in or along a first coronary vein overlying the left ventricle; (d) a fiducial sensing circuit operably coupled to the processor, wherein the fiducial sensing circuit is configured to receive input from one or more electrodes configured to sense a fiducial of electrical activity of the heart; and (e) a timing circuit operably coupled to the processor, wherein the timing circuit is configured to mark the timing of the fiducial of electrical activity of the heart.

An 18$^{th}$ aspect is a device comprising: (a) the computer readable medium the 14$^{th}$ aspect, (b) a processor capable of executing the instructions of the computer readable medium; (c) one or more local sensing circuits operably coupled to the processor, wherein the one or more sensing circuits are configured to receive input from one or more electrodes configured to sense electrical data from each of the plurality of locations in or along a first coronary vein overlying the left ventricle; (d) a pacing circuit operably coupled to the processor, wherein the pacing circuit is configured to provide an electrical pacing signal deliverable to a chamber of the heart; and (e) a timing circuit operably coupled to the processor, wherein the timing circuit is configured to mark the timing of delivery of the electrical pacing signal, wherein the timing of the pacing event is the timing of the fiducial.

A 19$^{th}$ aspect is a system comprising: (a) means for marking timing of a fiducial of electrical activity of the heart; (b) means for determining a myocardial activation time, relative to the timing of the fiducial, at each of a plurality of locations in or along a first coronary vein overlying a left ventricle; (c) means for determining an electrical dispersion for the first coronary vein, wherein determining the electrical dispersion comprises calculating the difference between (i) the activation time at the location that had the latest activation time of the plurality of locations and (ii) the activation time at the location that had the earliest activation time of the plurality of locations; (d) means for determining whether the magnitude of the electrical dispersion for the first vein meets or exceeds a predetermined threshold; and (e) means for indicating the first vein as the target vein for left ventricular lead placement if the electrical dispersion for the vein meets or exceeds a predetermined threshold.

A 20$^{th}$ aspect is a method for selecting a target vein for left ventricular lead placement for cardiac resynchronization therapy, comprising: (a) marking timing of a fiducial of electrical activity of the heart; (b) determining a myocardial activation time, relative to the timing of the fiducial, at each of a plurality of locations in or along a first coronary vein overlying a left ventricle; (c) determining an electrical dispersion for the first coronary vein by calculating the difference between (i) the activation time at the location that had the latest activation time of the plurality of locations and (ii) the activation time at the location that had the earliest activation time of the plurality of locations; (d) determining a myocardial activation time, relative to the timing of the fiducial, at each of a plurality of locations in or along a second coronary vein overlying a left ventricle; (e) determining an electrical dispersion for the second coronary vein, wherein determining the electrical dispersion comprises calculating the difference between (i) the activation time at the location that had the latest activation time of the plurality of locations and (ii) the activation time at the location that had the earliest activation time of the plurality of locations; (f) determining whether the magnitude of the electrical dispersion for the first vein is greater than the electrical dispersion for the second vein; and (g) identifying the first vein as the target vein for left ventricular lead placement if the electrical dispersion for the first vein is greater than the electrical dispersion for the second vein.

Computer readable media, devices, and systems capable of carrying out the method of the 20$^{th}$ aspect are described and contemplated herein.

EXAMPLES

In the following, non-limiting examples are presented, which describe studies and analysis supporting concepts, or aspects thereof, described herein.

Electrograms (EGMs) were recorded from within CS veins in ten patients. The baseline data collection for every patient included QRS duration, ejection fraction, LV dimensions, heart failure etiology, drug regimen and NYHA classification. The patients were studied in a fasting non-sedated state. Chronic medications were maintained until the initiation of the study. A patient was laid in the supine position and draped in a sterile fashion. ECG electrodes were attached to the body. Standard bipolar right atrial and right ventricular pace/sense catheters were inserted through the left subclavian vein into the right atrium (RA) and right ventricle (RV) respectively. Two properly balanced and calibrated micromanometer catheters (Millar Instruments, Houston, Tex., USA) were introduced into the RV and LV through small incisions in a femoral vein and femoral artery correspondingly. The coronary sinus was engaged via the left subclavian vein with a balloon occlusion guiding catheter. After assessing coronary vein distribution by occlusive venography, a multi-polar 2.5 Fr EP catheter was introduced into the marginal lateral or posterolateral coronary vein. This catheter (Cardima PATHFINDER intravascular mapping microcatheter) had eight 2 mm spaced electrode pairs (bipoles) with 8 mm distance between every two neighboring pairs. The catheter was advanced towards the heart's apex as far as possible. Three out of eight electrode pairs of the catheter were chosen for pacing the apical (Apex), middle (Mid) and basal (Base) parts of the LV free wall. The bipolar pacing thresholds from each of these three sites were obtained and documented. Pacing for the remainder of the study was performed at two times the threshold. Data were collected during biventricular pacing from RV electrode and each of the three CS sites, RV only pacing and intrinsic rhythm. Each rhythm was maintained at least for 1 minute, involving 60-80 beats. The timing of local activation via electrodes placed within various coronary sinus veins was determined relative to the earliest onset of QRS on ECG for intrinsic rhythm or relative to a right ventricular pacing event (with pacing from the apical wall of the right ventricle). Activation times were obtained at three sites within each vein (distal, mid and proximal) for each beat of a given rhythm. A mean activation time (over all beats) was computed for each site for a given rhythm. The effectiveness of left acute ventricular contraction (as measured by dP/dT max) was determined following bi-ventricular pacing, where left ventricular lead placement was in the various coronary sinus veins at the locations from which the local activation times were determined.

Figure 14:
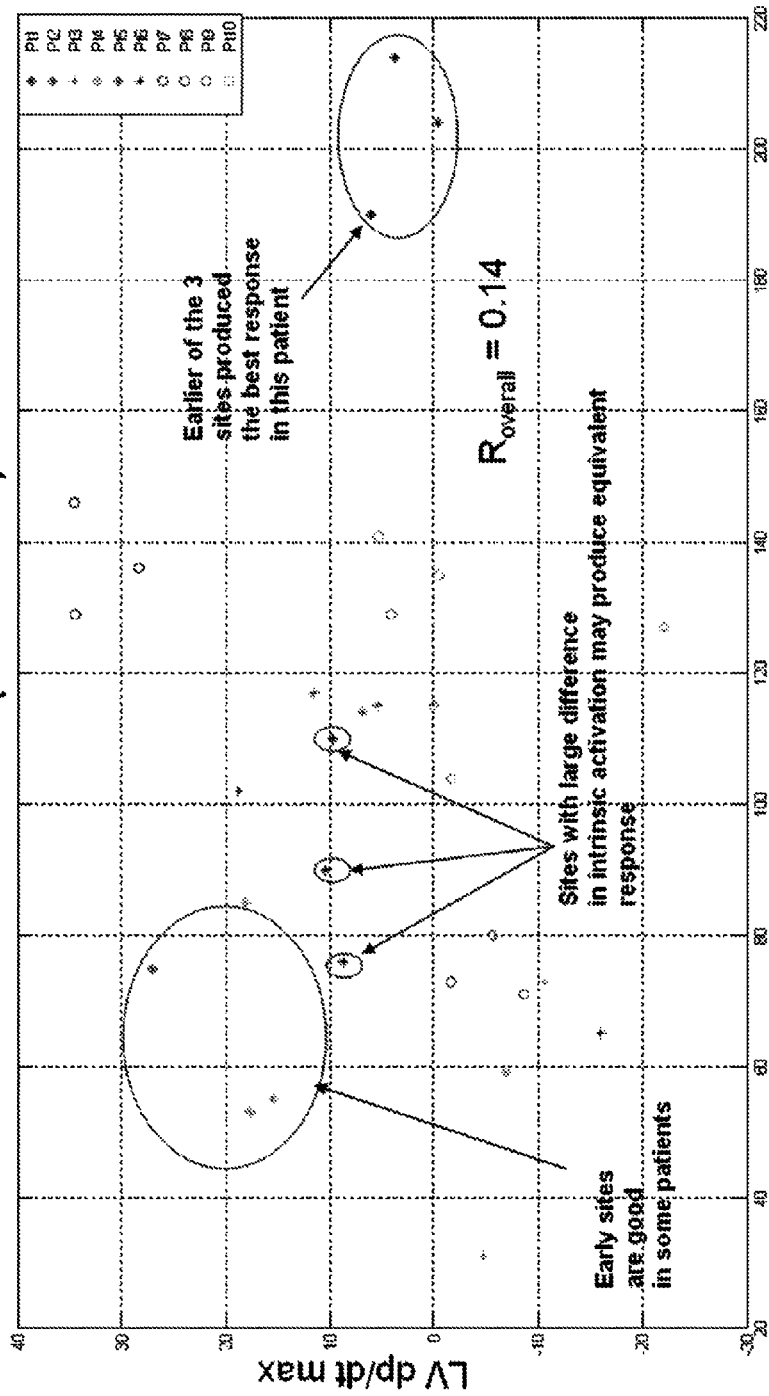
FIG. 14 is a plot of left ventricular pumping efficiency (dP/Dt max) of biventricular CRT over activation times measured in coronary veins of ten patients, in which veins left ventricular pacing leads for CRT were placed, following an intrinsic heart beat fiducial (NSR Activation Time, in milliseconds). "NSR" refers to "normal sinus rhythm," which is an electrogram of a normally beating heart.

A lack of consistent correlation between effectiveness of pacing (dP/dT max) and either intrinsic or RV-paced activation times was found. As shown in FIG. 14 the correlation coefficient of pacing efficiency and inactivation times at the site of left ventricular pacing across all ten patients was 0.14 ($R_{overall}$=0.14, Pearson correlation) As highlighted in the plot presented in FIG. 14, (i) sites of early activation were good sites for left ventricular pacing in some patients; (ii) within some individual patients, sites of earlier activation produced effective pacing; and (iii) within some patients, sites with large differences in intrinsic activation produced roughly equivalent pacing efficacy.

Figure 15:
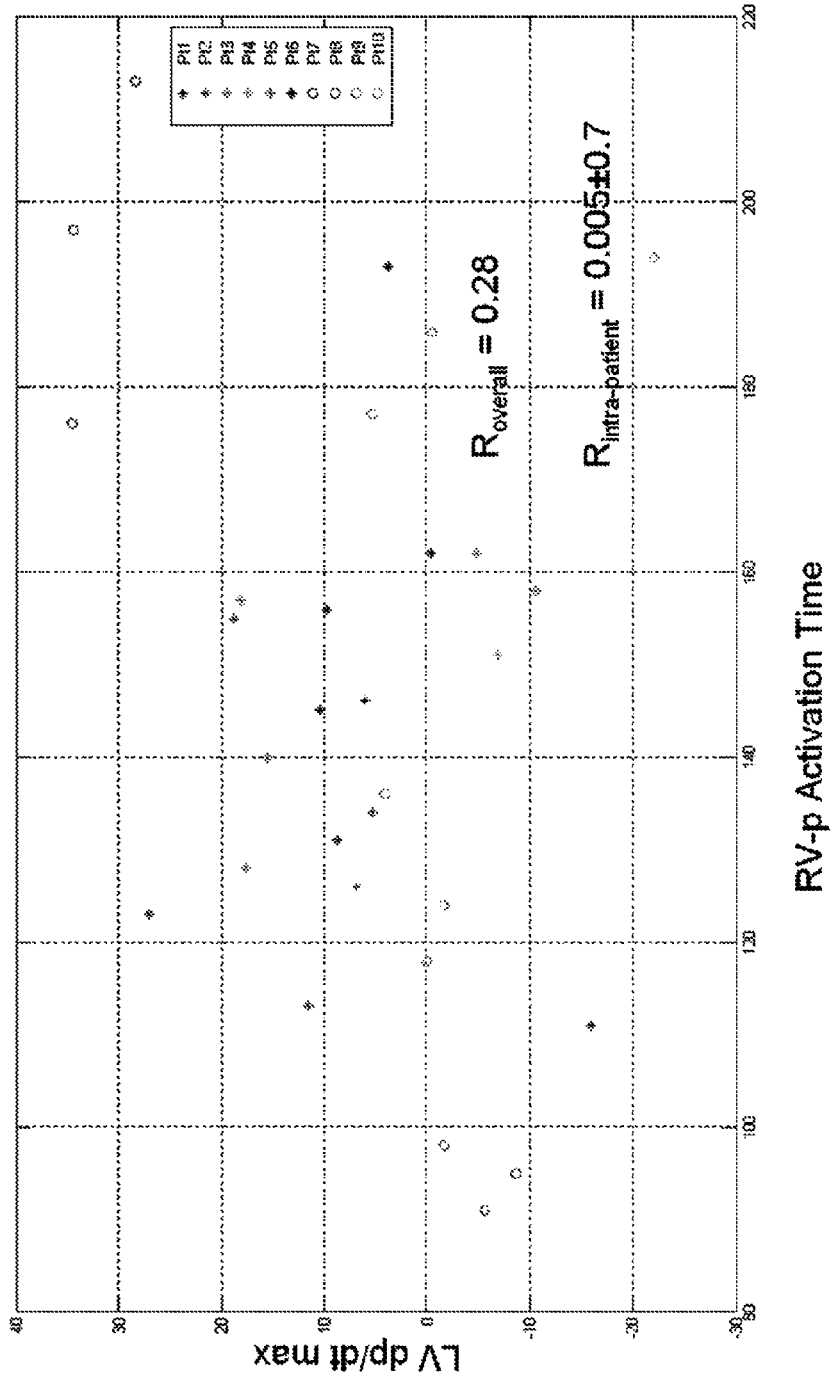
FIG. 15 is a plot of left ventricular pumping efficiency (dP/Dt max) of biventricular CRT over activation times measured in coronary veins of ten patients, in which veins left ventricular pacing leads for CRT were placed, following right ventricular pacing (RV-p Activation Time, in milliseconds).

As shown in FIG. 15, the correlation between pacing effectiveness and activation time following right ventricular pacing was poor. The correlation across all patients was 0.28 ($R_{overall}$=0.28). There was even less correlation within individual patients ($R_{intra-patient}$=0.005±0.7).

Figure 16:
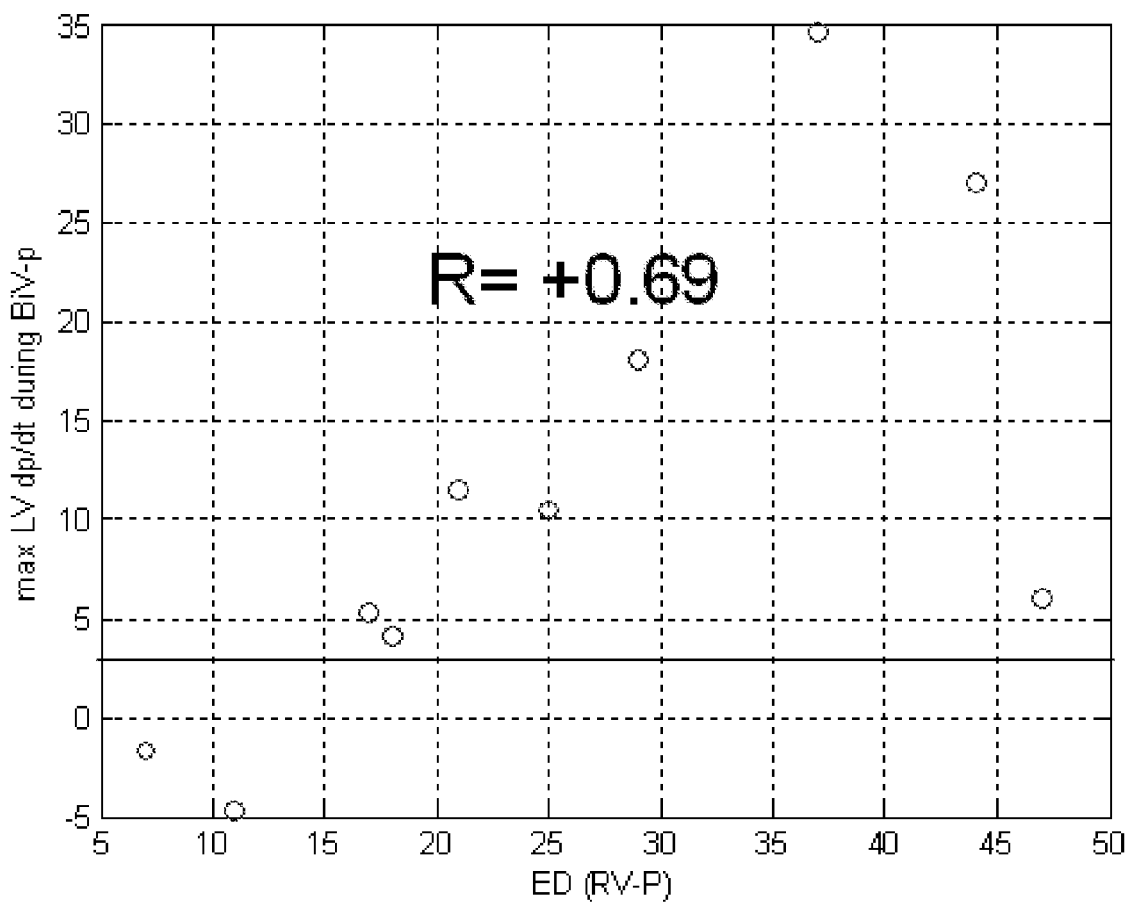
FIG. 16 is a is a plot of left ventricular pumping efficiency (dP/Dt max) of biventricular CRT over electrical dispersion values measured in coronary veins of ten patients, in which veins left ventricular pacing leads for CRT were placed, following right ventricular pacing (ED RV-P).

In contrast, magnitude of electrical dispersion (or electrical dyssynchrony) of activation times within a vein (for right ventricular pacing) did correlate well with pacing efficacy (see FIG. 16, $R_{overall}$=0.69). Veins with greater acute dispersion (n=8) produced a greater left ventricular acute response, while veins with minimal electrical dispersion (n=2) during right ventricular pacing did not produce a positive dP/dT change during biventricular pacing. The data supports the hypothesis and the idea that a good vein for the coronary sinus lead may be one which contains a large dispersion of activation times during right ventricular pacing. In other words, a good target site for the coronary sinus left ventricular lead might be a vein with the high degree of regional electrical dyssynchrony during right ventricular pacing, rather than the site which is electrically latest. Selection of a 'good' responsive vein may be more important than selection of a particular site within a vein, because a previous study has shown no significant differences in hemodynamic effects among different stimulation sites within a given coronary vein (see, Gold MR, et al. Comparison of stimulation sites within LV veins on the acute hemodynamic effects of cardiac resynchronization therapy. Heart Rhythm 2005; 2:376-381).

Figure 17:
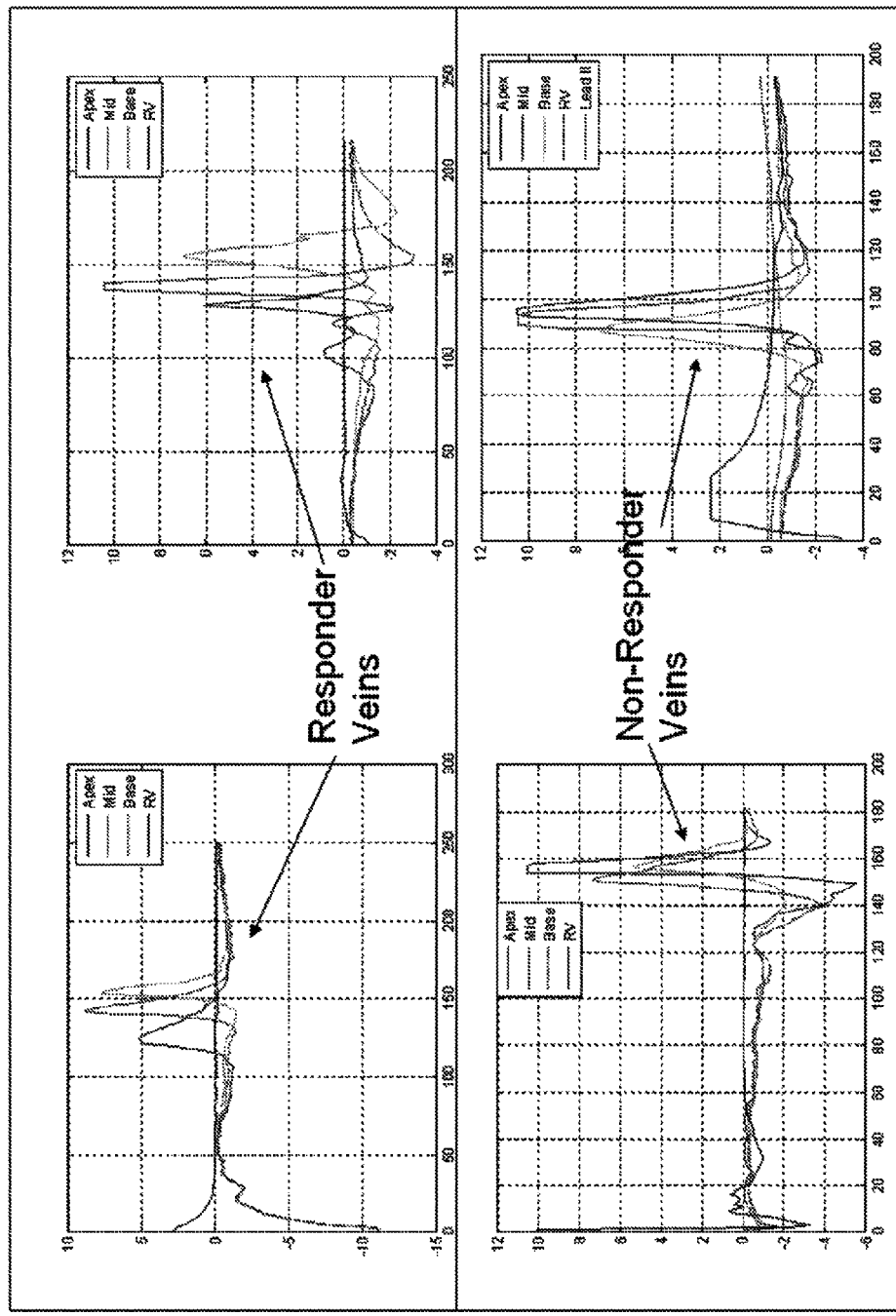
FIG. 17 shows plots of electrograms of electrical activity at various locations (distal or "apex", mid, and proximal or "base") of coronary veins of patients over time, which selected veins representing left ventricular coronary sinus veins in which effective biventricular CRT was observed (upper panels, "Responder Veins") and in which ineffective biventricular CRT was observed (lower panels, "Non-Responder Veins").

Another potential predictive indicator of pacing efficacy is sequential activation times within a vein. FIG. 17 depicts representative examples of EGMs recorded at a distal portion of a vein (apex), a mid portion of a vein (mid), and a proximal portion of a vein (base) in veins that produced effective bi-ventricular pacing (as measured by dP/dT), "responder veins" (upper right and upper left panels), and veins that did not produce effective bi-ventricular pacing, "non-responder veins" (lower right and lower left panels). A particular vein was judged as a responder vein if biventricular stimulation at any one site within a vein produced a dp/dt max greater than 0% (and non-responder is dp/dt max was less than 0%).

Left ventricular pacing from veins in which activation times occurred sequentially from apex to base (apex to mid to base) during right ventricular pacing (upper panels) resulted in effective bi-ventricular pacing. However, left ventricular pacing in veins that did not show such sequential activation times (lower panels) resulted in poor pacing efficacy. In the non-responder vein depicted in the lower left panel, the sequence of activation time was mid-base-apex. In the non-responder vein depicted in the lower left panel, the sequence of activation time was base-mid-apex. This data supports the hypothesis and idea that veins that exhibit sequential activation times from apex to base may be good candidate veins for left ventricular lead placement for bi-ventricular pacing. Such sequential activation time may also be used in combination with electrical dispersion within a vein to identify suitable target veins for left ventricular pacing.

Figure 18:
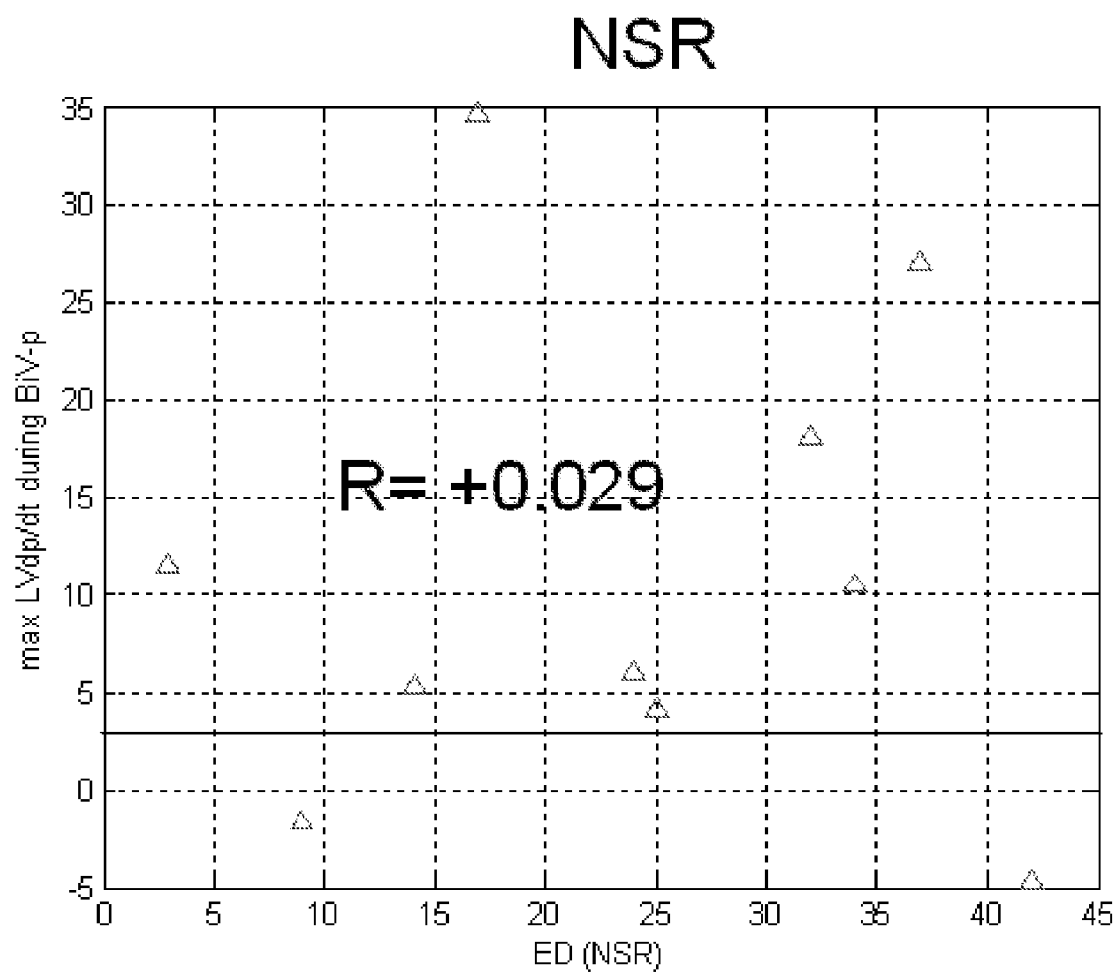
FIG. 18 is a plot of left ventricular pumping efficiency (dP/Dt max) of biventricular CRT over electrical dispersion values measured in coronary veins of ten patients, in which veins left ventricular pacing leads for CRT were placed, following an intrinsic heart beat fiducial (ED NSR).

It should be noted that magnitude of electrical dispersion of activation times within a vein (for intrinsic rhythm) did not correlate well with pacing efficacy (see FIG. 18, $R_{overall}$=0.029). However, it is believed that magnitude of electrical dispersion within a vein would be a good predictor for left ventricular pacing only, as opposed to bi-ventricular pacing as done in this study. For example, because the pacing that determined pacing efficacy (dP/dT) in this study was bi-ventricular pacing, it follows that electrical dispersion associated with right ventricular pacing was a good predictor because right ventricular pacing is performed in bi-ventricular pacing and it is believed that choosing the vein with the greatest electrical dispersion during RV only pacing allows optimal fusion of the right and left paced activations during biventricular pacing. However, for left ventricular only pacing, intrinsic activation times may be important because optimal fusion of right ventricular intrinsic activity is desired for left ventricular only pacing.

Thus, systems, devices and methods for DETECTION OF TARGET VEIN FOR CRT THERAPY are described. Those skilled in the art will recognize that the preferred embodiments described herein may be altered or amended without departing from the true spirit and scope of the disclosure, as defined in the accompanying claims.

The invention claimed is:

1. A method for selecting a target vein for left ventricular lead placement for cardiac resynchronization therapy, comprising:
   marking timing of a fiducial of electrical activity of the heart;
   determining a myocardial activation time, relative to the timing of the fiducial, at each of a plurality of locations in or along a first coronary vein overlying a left ventricle;
   determining an electrical dispersion for the first coronary vein, wherein determining the electrical dispersion comprises calculating the difference between (i) the activation time at the location that had the latest activation time of the plurality of locations and (ii) the activation time at the location that had the earliest activation time of the plurality of locations;

determining whether the magnitude of the electrical dispersion for the first vein meets or exceeds a predetermined high threshold; and identifying the first vein as the target vein for left ventricular lead placement if the electrical dispersion for the vein meets or exceeds the predetermined high threshold.

2. The method of claim 1, wherein marking timing of the fiducial of electrical activity of the heart comprises marking the timing electrical activity selected from the group consisting of a fiducial of pacing or a fiducial of an intrinsic sinus rhythm.

3. The method of claim 1, wherein marking timing of the fiducial of electrical activity of the heart comprises marking the timing of electrical activity selected from the group consisting of pacing of a right ventricle, a peak of an R-wave, and onset of QRS.

4. The method of claim 1, wherein determining the myocardial activation time, relative to the timing of the fiducial, at each of the plurality of locations in or along the first coronary vein comprises correlating a map of activation times across the heart to an image of the heart in which the first coronary vein is detectable, and identifying the activation time at each of the plurality of locations in or along the first coronary vein.

5. The method of claim 1, wherein determining the myocardial activation time, relative to the timing of the fiducial, at each of the plurality of locations in or along the first coronary vein comprises sensing activation via a plurality of electrodes of a lead, wherein at least one electrode of the lead is positioned at each of the plurality of locations in or along the first coronary vein.

6. The method of claim 1, wherein determining the myocardial activation time, relative to the timing of the fiducial, at each of the plurality of locations in or along the first coronary vein comprises:

(a) sensing activation, via an electrode of a lead, at one of the plurality of locations in or along the first coronary vein;

(b) moving the electrode to another of the plurality of locations in or along the first coronary vein and sensing activation via the electrode at the other location; and (c) repeating step (b), if necessary, until activation has been sensed at each of the plurality of locations in or along the first coronary vein.

7. The method of claim 1, wherein, if the electrical dispersion for the first vein is determined to not meet or exceed the predetermined threshold, the method further comprises:

marking timing of the fiducial of electrical activity of the heart;

determining a myocardial activation time, relative to the timing of the fiducial, at each of a plurality of locations in or along a second coronary vein overlying the left ventricle;

determining an electrical dispersion for the second coronary vein by calculating the difference between (i) the activation time at the location that had the latest activation time of the plurality of locations and (ii) the activation time at the location that had the earliest activation time of the plurality of locations;

determining whether the magnitude of the electrical dispersion for the second vein meets or exceeds the predetermined high threshold; and identifying the second vein as the target vein for left ventricular lead placement if the electrical dispersion for the vein meets or exceeds the predetermined high threshold.

8. The method of claim 1, further comprising determining whether the magnitude of the electrical dispersion for the first vein meets or exceeds a predetermined mid threshold; and identifying the first vein as a possible target vein for left ventricular lead placement if the electrical dispersion for the vein meets or exceeds the predetermined mid threshold, but not the predetermined high threshold.

9. The method of claim 1, further comprising determining whether the magnitude of the electrical dispersion for the first vein meets or exceeds a predetermined low threshold; and excluding the first vein as the target vein for left ventricular lead placement if the electrical dispersion for the vein does not meet or exceed the predetermined low threshold.

10. The method of claim 1, wherein the plurality of locations in or along the first vein comprises three or more locations.

11. A method carried out by a device configured to assist in selecting a target vein for left ventricular lead placement for cardiac resynchronization therapy, comprising:

receiving input regarding timing of a fiducial of electrical activity of the heart;

receiving input regarding local electrical activity at a plurality of locations in or along a first coronary vein overlaying a left ventricle;

determining a myocardial activation time, relative to the timing of the fiducial, of each of the plurality of locations in or along the first coronary vein;

determining an electrical dispersion for the first coronary vein, wherein determining the electrical dispersion comprises calculating the difference between (i) the activation time at the location that had the latest activation time of the plurality of locations and (ii) the activation time at the location that had the earliest activation time of the plurality of locations; and determining whether the magnitude of the electrical dispersion for the first vein meets or exceeds a predetermined threshold.

12. The method of claim 11, further comprising outputting data indicating whether the threshold was met or exceeded.

13. The method of claim 12 wherein outputting the data comprises outputting a value of the magnitude of the electrical dispersion of the first vein.

14. A non-transitory computer readable medium for a system configured to identify a target vein for left ventricular lead placement for cardiac resynchronization therapy, the computer readable medium comprising instructions that, when implemented, cause the system to:

mark timing of a fiducial of electrical activity of the heart;

determine a myocardial activation time, relative to the timing of the fiducial, at each of a plurality of locations in or along a first coronary vein overlying a left ventricle;

determine an electrical dispersion for the first coronary vein by calculating the difference between (i) the activation time at the location that had the latest activation time of the plurality of locations and (ii) the activation time at the location that had the earliest activation time of the plurality of locations;

determine whether the magnitude of the electrical dispersion for the first vein meets or exceeds a predetermined threshold; and indicate the first vein as the target vein for left ventricular lead placement if the electrical dispersion for the first vein meets or exceeds a predetermined threshold.

15. A system comprising:
the computer readable medium of claim 14,
electronics capable of executing the instructions of the computer readable medium;
one or more electrodes configured to sense electrical data from each of the plurality of locations in or along a first coronary vein overlying the left ventricle and to provide the electronics with the sensed data;
one or more electrodes configured to sense a fiducial of electrical activity of the heart and configured to provide data regarding the fiducial to the electronics.

16. A system comprising:
the computer readable medium of claim 14,
electronics capable of executing the instructions of the computer readable medium;
one or more electrodes configured to sense electrical data from each of the plurality of locations in or along a first coronary vein overlying the left ventricle and to provide the electronics with the sensed data;
a memory configured to record timing of a pacing event of the heart and to provide data regarding the timing of the pacing event to the electronics, wherein the timing of the pacing event is the timing of the fiducial.

17. A device comprising:
the computer readable medium of claim 14,
a processor capable of executing the instructions of the computer readable medium;
one or more local sensing circuits operably coupled to the processor, wherein the one or more sensing circuits are configured to receive input from one or more electrodes configured to sense electrical data from each of the plurality of locations in or along a first coronary vein overlying the left ventricle;
a fiducial sensing circuit operably coupled to the processor, wherein the fiducial sensing circuit is configured to receive input from one or more electrodes configured to sense a fiducial of electrical activity of the heart; and
a timing circuit operably coupled to the processor, wherein the timing circuit is configured to mark the timing of the fiducial of electrical activity of the heart.

18. A device comprising:
the computer readable medium of claim 14,
a processor capable of executing the instructions of the computer readable medium;
one or more local sensing circuits operably coupled to the processor, wherein the one or more sensing circuits are configured to receive input from one or more electrodes configured to sense electrical data from each of the plurality of locations in or along a first coronary vein overlying the left ventricle;
a pacing circuit operably coupled to the processor, wherein the pacing circuit is configured to provide an electrical pacing signal deliverable to a chamber of the heart; and
a timing circuit operably coupled to the processor, wherein the timing circuit is configured to mark the timing of delivery of the electrical pacing signal, wherein the timing of the pacing event is the timing of the fiducial.

19. A system comprising
means for marking timing of a fiducial of electrical activity of the heart;
means for determining a myocardial activation time, relative to the timing of the fiducial, at each of a plurality of locations in or along a first coronary vein overlying a left ventricle;
means for determining an electrical dispersion for the first coronary vein, wherein determining the electrical dispersion comprises calculating the difference between (i) the activation time at the location that had the latest activation time of the plurality of locations and (ii) the activation time at the location that had the earliest activation time of the plurality of locations;
means for determining whether the magnitude of the electrical dispersion for the first vein meets or exceeds a predetermined threshold; and
means for indicating the first vein as the target vein for left ventricular lead placement if the electrical dispersion for the vein meets or exceeds a predetermined threshold.

20. A method for selecting a target vein for left ventricular lead placement for cardiac resynchronization therapy, comprising:
marking timing of a fiducial of electrical activity of the heart;
determining a myocardial activation time, relative to the timing of the fiducial, at each of a plurality of locations in or along a first coronary vein overlying a left ventricle;
determining an electrical dispersion for the first coronary vein, wherein determining the electrical dispersion comprises calculating the difference between (i) the activation time at the location that had the latest activation time of the plurality of locations and (ii) the activation time at the location that had the earliest activation time of the plurality of locations;
determining a myocardial activation time, relative to the timing of the fiducial, at each of a plurality of locations in or along a second coronary vein overlying a left ventricle;
determining an electrical dispersion for the second coronary vein by calculating the difference between (i) the activation time at the location that had the latest activation time of the plurality of locations and (ii) the activation time at the location that had the earliest activation time of the plurality of locations;
determining whether the magnitude of the electrical dispersion for the first vein is greater than the electrical dispersion for the second vein; and
identifying the first vein as the target vein for left ventricular lead placement if the electrical dispersion for the first vein is greater than the electrical dispersion for the second vein.

* * * * *